(12) United States Patent
Mattoussi et al.

(10) Patent No.: US 9,580,560 B2
(45) Date of Patent: Feb. 28, 2017

(54) POLYMER LIGANDS FOR NANOPARTICLES

(71) Applicant: The Florida State University Research Foundation, Inc., Tallahassee, FL (US)

(72) Inventors: Hedi Mattoussi, Tallahassee, FL (US); Wentao Wang, Tallahassee, FL (US); Goutam Palui, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 4 days.

(21) Appl. No.: 14/672,436

(22) Filed: Mar. 30, 2015

(65) Prior Publication Data

US 2015/0284517 A1    Oct. 8, 2015

Related U.S. Application Data

(60) Provisional application No. 61/974,122, filed on Apr. 2, 2014.

(51) Int. Cl.

| | |
|---|---|
| *C08F 8/32* | (2006.01) |
| *C08G 81/02* | (2006.01) |
| *C09D 123/36* | (2006.01) |
| *C09D 187/00* | (2006.01) |
| *G01N 33/50* | (2006.01) |
| *G01N 33/58* | (2006.01) |
| *C09D 135/00* | (2006.01) |

(52) U.S. Cl.
CPC ............... *C08G 81/025* (2013.01); *C08F 8/32* (2013.01); *C09D 123/36* (2013.01); *C09D 187/005* (2013.01); *G01N 33/5005* (2013.01); *G01N 33/582* (2013.01); *C09D 135/00* (2013.01)

(58) Field of Classification Search
None
See application file for complete search history.

(56) References Cited

U.S. PATENT DOCUMENTS

2005/0032929 A1*  2/2005  Greener ................... C08F 8/00
                                                         523/113
2005/0201974 A1*  9/2005  Schestopol ........... A61K 9/0065
                                                         424/78.27

OTHER PUBLICATIONS

Na, ACS Nano, 2012, 6(1), pp. 389-399.*
Alivisatos, A.P., Semiconductor Clusters, Nanocrystals, and Quantum Dots, Science; Feb. 16, 1996, vol. 271, No. 5251; ProQuest; pp. 933-937.

(Continued)

*Primary Examiner* — Robert C Boyle
(74) *Attorney, Agent, or Firm* — Armstrong Teasdale LLP

(57) ABSTRACT

The disclosure is directed to polymer ligands that are optimally suited for surface-functionalizing magnetic nanoparticles. The amphiphilic polymers are prepared by coupling several amine-terminated anchoring groups, polyethylene glycol moieties, and reactive groups onto a poly (isobutylene-alt-maleic anhydride) (PIMA) chain. The reaction of maleic anhydride groups with amine-containing molecules is highly-efficient and occurs in one-step. The availability of several dopamine groups in the same ligand greatly enhances the ligand affinity, via multiple-coordination, to the magnetic NPs, while the hydrophilic and reactive groups promote colloidal stability in buffer media and allow subsequent conjugation with target biomolecules. Nanoparticles ligated with terminally reactive polymers have been easily coupled to target dyes and tested in live cell imaging with no measurable cytotoxicity.

14 Claims, 6 Drawing Sheets

(56) References Cited

OTHER PUBLICATIONS

Murray, C. B., et al., Synthesis and Characterization of Monodisperse Nanocrystals and Close-Packed Nanocrystal Assemblies, Annu. Rev. Mater. Sci, 2000, vol. 30 pp. 545-610.
Klimov, V.I. et al., Optical Gain and Stimulated Emission in Nanocrystal Quantum Dots, Science, Oct. 13, 2000, vol. 290, No. 5490; ProQuest, pp. 314-317.
Malko, A.V. et al., From amplified spontaneous emission to microring lasing using nanocrystal quantum dots solids, Applied Physcis Letters, Aug. 12, 2002, vol. 81, No. 7, pp. 1303-1305.
Nozik, A. J. et al., Semiconductor Quantum Dots and Quantum Dot Arrays and Applications of Multiple Exciton Generation to Third-Generation Photovoltaic Solar Cells, Chem. Rev., 2010, vol. 110, pp. 6873-6890.
Li Ling et al., Highly Efficient CdS Quantum Dot-Sensitized Solar Cells Based on a Modified Polysulfide Electrolyte, Journal of the American Chemical Society, 2011, vol. 133, pp. 8458-8460.
Raymo, Francisco M., et al., Luminescent chemosensors based on semiconductor quantum dots, Physical Chemistry Chemical Physics, Feb. 1, 2007, vol. 9, pp. 2036-2043.
Medintz, Igor L., et al., Quantum dot bioconjugates for imaging labelling and sensing, Nature Materials, Jun. 2005, vol. 4, pp. 435-446.
Michalet, X. et al., Quantum Dots for Live Cells, in Vivo Imaging, and Diagnostics, Science, Jan. 28, 2005, vol. 307, pp. 538-544.
Biju, Vasudevanpillai et al., Delivering quantum dots to cells: bioconjugated quantum dots for targeted and nonspecific extracellular and intracellular imaging, Chemical Society Reviews, May 27, 2010, vol. 39, pp. 3031-3056.
Zrazhevskiy, Paul et al., Designing multifunctional quantum dots for bioimaging, detection, and drug delivery, Chemical Society Reviews, Dec. 23, 2009, vol. 39, pp. 4326-4354.
Pinaud, Fabien et al., Probing cellular events, one quantum dot at a time, Nature Methods, Apr. 2010, vol. 7, No. 4, pp. 275-285.
Jaiswal, Jyoti K. et al., Long-term multiple color imaging of live cells using quantum dot bioconjugates, Nature Biotechnology, Jan. 2003, vol. 21, pp. 47-51.
Gao, Xiaohu, et al., In vivo cancer targeting and imaging with semiconductor quantum dots, Nature Biotechnology, Aug. 2004, vol. 22, No. 8, pp. 969-976.
Rossetti, R. et al., Size effects in the excited electronic states of small colloidal CdS crystallites, Journal of Chemical Physics, 1984, vol. 80, pp. 4464-4469.
Murray, C. B. et al., Synthesis and Characterization of Nearly Monodisperse CdE (E=S, Se, Te) Semiconductor Nanocrystallites, American Chemical Socity, 1993, vol. 115, pp. 8706-8715.
Dabbousi, B. O. et al., (CdSe)Zns Core-Shell Quantum Dots: Synthesis and Characterization of a Size Series of Highly Luminescent Nanocrystallites, 1997, vol. 101, pp. 9463-9475.
Liu, Wenhao et al., Compact Biocompatible Quantum Dots Functionalized for Cellular Imaging, Journal of American Chemical Society, 2008, vol. 130, pp. 1274-1284.
Susumu, Kimihiro et al., Multifunctional ligands based on dihydrolipoic acid and polyethylene glycol to promote biocompatibility of quantum dots, Nature Protocols, 2009, vol. 4, No. 3, pp. 424-436.
Jung, Jongjin et al., Selective Inhibition of Human Tumor Cells through Multifunctional Quantum-Dot-Based siRNA Delivery, Angew. Chem. Inc. Ed., 2010, vol. 49, pp. 103-107.
Liu, Wenhao et al., Compact Biocompatible Quantum Dots via RAFT-Mediated Synthesis of Imidazole-Based Random Copolymer Lignad, American Chemical Society, 2010, vol. 132, pp. 472-483.
Lee, Jae-Hyun et al., Artificially engineered magnetic nanoparticles for ultra-sensitive molecular imaging, Jan. 2007, vol. 13, No. 1, pp. 95-99.
Stewart, Michael H. et al., Multidentate Poly(ethylene glycol) Ligands Provide Colloidal Stability to Semiconductor and Metallic Nanocrystals in Extreme Conditions, Journal of American Chemical Society, 2010, vol. 132, pp. 9804-9813.
Muro, Eleonora et al., Small and Stable Sulfobetaine Zwitterionic Quantum Dots for Functional Live-Cell Imaging, Journal of American Chemical Society, 2010, vol. 132, pp. 4556-4557.
Less, Emma E. et al., Experimental Determination of Quantum Dot Size Distributions, Ligand Packing Densities, an Bioconjugation Using Analytical Ultracentrifugation, American Chemical Society, 2008, vol. 8, No. 9, pp. 2883-2890.
Liu, Lu et al., Bifunctional Multidentate Ligand Modified Highly Stable Water-Soluble Quantum Dots, Inorganic Chemistry, American Chemical Society, 2010, vol. 49, pp. 3768-3775.
Clapp, Aaron R. et al., Capping of CdSe—ZnS quantum dots with DHLA and subsequent conjugation with proteins, Nature Protocols, 2006, vol. 1, No. 3, pp. 1258-1266.
Qu, Lianhua et al., Alternative Routes toward High Quality CdSe Nanocrystals, American Chemical Society, 2001, vol. 1, No. 6, pp. 333-337.
Mei, Bing C., Modular poly(ethylene glycol) ligands for biocompatible semiconductor and gold nanocrystals with extended pH and ionic stability, J. Mater. Chem., 2008, vol. 18, pp. 4949-4958.
Uyeda, Tetsuo H. et al., Synthesis of Compact Multidentate Ligands to Prepare Stable Hydrophilic Quantum Dot Fluorophores, Journal of American Chemical Society, 2005, vol. 127, pp. 3870-3878.
Choi, Chung Hang J., et al., Mechanism of active targeting in solid tumors with transferrin-containing gold nanoparticles, PNAS, Jan. 19, 2010, vol. 107, No. 3, 1235-1240.
Clapp, Aaron R. et al., Fluorescence Resonance Energy Transfer Between Quantum Dot Donors, Journal of American Chemical Society, 2004, vol. 126, pp. 301-310.
Medintz, Igor L., et al., Proteolytic activity monitored by fluorescence resonance energy transfer through quantumdot-peptide conjugates, Nature Materials, Jul. 2006, vol. 5, pp. 581-589.
Chen, Chun-Yen et al., Potassium ion recognition by 15-crown-5 functionalized CdSe/ZnS quantum dots in H2O, Chem. Commun, 2006, pp. 263-265.
Susumu, Kimihiro et al., Colloidal Quantum Dots: Synthesis, Photophysical Properties, and Biofunctionalization Strategies, Atrech House, Aug. 25, 2008, pp. 1-26.
Hines, Margaret A., et al., Synthesis and Characterization of Strongly Luminescing ZnS-Capped CdSe Nanocrystals, J. Phys. Chem, American Chemical Society, 1996, vol. 100, No. 2, pp. 468-471.
Van Embden, Joel et al., Mapping the Optical Properties of CdSe/CdS Heterostructure Nanocrystals: The Effects of Core Size and Shell Thickness, Journal of American Chemical Society, 2009, vol. 131, pp. 14299-14309.
Gerion, Daniele, et al., Synthesis and Properties of Biocompatible Water-Soluble Silica-Coated CdSe/ZnS Semicondutor Quantum Dots, J. Phys. Chem. B, 2001, vol. 105, pp. 8861-8871.
Bhang, Suk Ho et al., Hyaluronic Acid-Quantum Dot Conjugates for In Vivo Lymphatic Vessel Imaging, American Chemical Society, May 28, 2009, vol. 3, No. 6, pp. 1389-1398.
Yildiz, Ibrahim et al., Biocompatible CdSe-ZnS Core-Shell Quantum Dots Coated with Hydrophilic Polythiols, American Chemical Society, 2009, vol. 25, No. 12, pp. 7090-7096.
Yildiz, Ibrahim et al., Biocompatible CdSe—ZnS Core-Shell Quantum Dots with Reactive Function Groups on Their Surface, Langmuir, 2010, vol. 26, No. 13, pp. 11503-11511.
Shen, Hongyan et al., Poly(ethylene glycol) Carbondiimide Coupling Reagents for the Biological and Chemical Functionalization of Water-Soluble Nanoparticles, American Chemical Society, 2009, vol. 3, No. 4, pp. 915-923.
Anderson, Robin E. et al., Systematic Investigation of Preparing Biocompatible, Single, and Small ZnS-Capped CdSe Quantum Dots with Amphiphilic Polymers, American Chemical Society, 2008, vol. 2, No. 7, pp. 1341-1352.
Bullen, C. et al., The Effects of Chemisorption on the Luminescence of CdSe Quantum Dots, Langmuir, 2006, vol. 22, pp. 3007-3013.
Munro, Andrea M. et al., Quantitative Study of the Effects of Surface Ligand Concentration on CdSe Nanocrystal Photoluminescence, J. Phys. Chem. C, 2007, vol. 111, pp. 6220-6227.

(56) References Cited

OTHER PUBLICATIONS

Mei, Bing C. et al., Effects of Ligand Coordination Number and Surface Curvature on the Stability of Gold Nanoparticles in Aqueous Solutions, Langmuir, American Chemical Society, 2009, vol. 25, No. 18, pp. 10604-10611.

Na, Hyon Bin et al., Multidentate Catechol-Based Polyethylene Glycol Oligomers Provide Enhanced Stability and Biocompatibility to Iron Oxide Nanoparticles, American Chemical Society, 2012, vol. 6, No. 1, pp. 389-399.

Yu, William W. et al., Forming Biocompatible and Nanaggregated Nanocrystals in Water Using Amphiphilic Polymers, Article, Feb. 20, 2007, pp. 2871-2879, vol. 129, J. Am. Chem. Soc.

Palui, Goutam et al., Poly(ethylene glycol)-Based Multidentate Oligomers for Biocompatible Semiconductor and Gold Nanocrystals, Article, 2011, pp. 2761-2772, vol. 28, Langmuir, American Chemical Society.

Pellegrino, Teresa et al., Hydrophobic Nanocrystals Coated with an Amphiphilic Polymer Shell: A General Route to Water Soluble Nanocrystals, NANO letters, 2004, pp. 703-707, vol. 4, No. 4, American Chemical Society.

\* cited by examiner

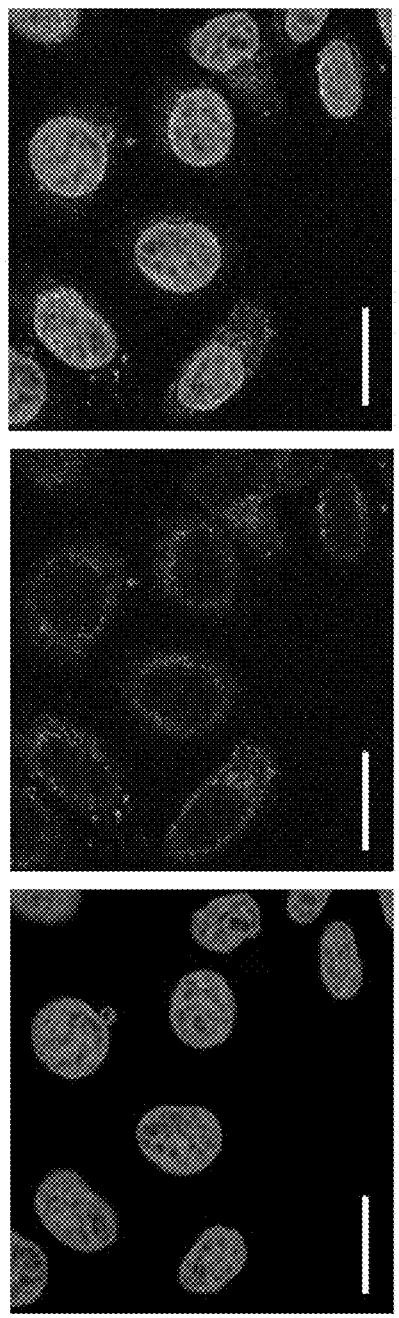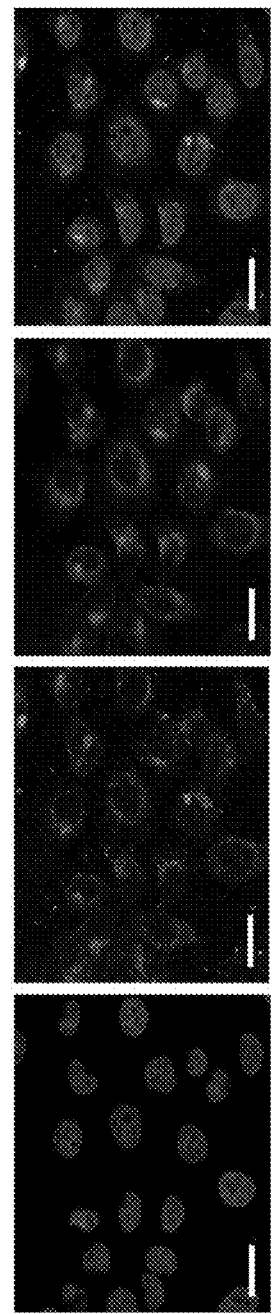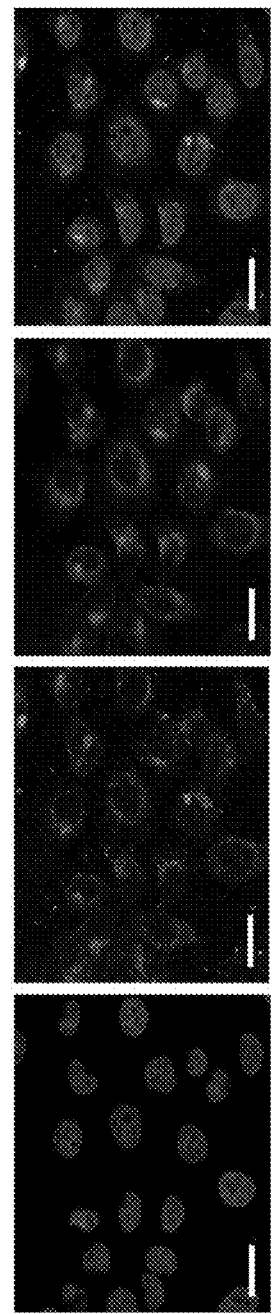

POLYMER LIGANDS FOR NANOPARTICLES

CROSS REFERENCE TO RELATED APPLICATIONS

This application claims priority from U.S. Provisional Application Ser. No. 61/974,122 filed Apr. 2, 2014, the disclosure of which is incorporated herein as if set forth in its entirety.

STATEMENT REGARDING FEDERALLY SPONSORED RESEARCH OR DEVELOPMENT

This invention was made with government support under NSF-CHE #1058957 awarded by the National Science Foundation. The government has certain rights in the invention.

FIELD OF THE INVENTION

The present invention relates to a polymer ligand suitable for coordinating with a nanoparticle.

BACKGROUND OF THE INVENTION

Magnetic nanoparticles such as those made of $Fe_3O_4$, FePt, Co, or Mn-doped $Fe_3O_4$ exhibit unique size- and composition-dependent physical properties that are not observed at the molecular scale or shared by their bulk parent materials. See references 1-7. This has generated a great deal of interest to integrate them into electronic devices and as contrast enhancement agents for Magnetic Resonance Imaging (MRI). See references 1-4, 6, and 7. Other potential applications in biology include use as magnetic carriers for drug delivery platforms, biosensors, hyperthermia and bioseparation. See references 8-13. Magnetic NPs as contrast enhancing agents for MR imaging and sensing have generated considerable attention and much work in the past decade. This has motivated researchers to develop new synthetic schemes to prepare large quantities of high quality magnetic nanoparticles and to conceive new surface-functionalization strategies for post growth manipulation and processing.

An effective integration of magnetic NPs into biology requires the availability of NPs with homogenous composition, reduced size distribution, high coercivity, and the ability to interface them with biological systems. Thus far, the most successful route to prepare high quality iron oxide (IO) nanoparticles (NP) with controllable size and high crystallinity has relied on the thermal decomposition of metal precursors (such as iron oleate, iron pentacarbonyl and iron acetylacetonate) in hot surfactant solution. See references 14-18. However, nanocrystals synthesized via thermolysis of organometallic precursors are capped with hydrophobic ligands, which make them dispersible only in organic solvents. Therefore, any use in bio-inspired investigations requires additional chemical manipulation and post growth surface modification to render the magnetic NPs colloidally stable in buffer media and biocompatible. See references 4 and 19-22.

Two main strategies have emerged as reliable approaches for interfacing these materials with biological systems. One uses amphiphilic polymers (e.g., copolymers and phospholipids) to encapsulate the as-prepared hydrophobic nanoparticles within micelle-like structures; it relies on the interdigitation (an entropy-driven process) between the hydrophobic segments of the polymers and the native cap. Such strategy has been employed by several groups to prepare various water-soluble NPs and to couple them to biomolecules. See references 23-30. Encapsulation preserves the native organic cap, which may be beneficial as this can better preserve the physical properties of the native materials (e.g., optical or magnetic), but tends to significantly increase the hydrodynamic size of the nanoparticles and may yield more than one nanocrystal per micelle. See references 23 and 30. This will limit their use in applications requiring small size probes. The other strategy relies on the removal of the hydrophobic shell and replacing it with bifunctional ligands that present anchoring groups and hydrophilic moieties: ligand exchange. These anchors interact with the metal surface via Lewis-base type coordination. This route should, in principle, provide compact NPs and better colloidal stability in physiological conditions, if the ligands present strong anchoring groups to NP surfaces. For $Fe_3O_4$ and $\gamma$-$Fe_2O_3$ magnetic nanocrystals, dopamine has been reported to exhibit specific affinity to the NP surface, a feature attributed to the improved orbital overlap of five-membered catechol ring and reduced steric effects. See references 9 and 31.

Several monodentate dopamine-modified ligands, such as dopamine-PEG-carboxy/amine and zwitterionic dopamine sulfonate have been used for preparing colloidal dispersions of iron oxide NPs in water media, due to ease of implementation. See references 32 through 34. Similarly, ligation with monodentate moieties has been applied to transfer a wide range of inorganic nanocrystals (e.g., metal NPs and quantum dots) to buffer media. However, the binding affinity of such monodentate ligands to the NP surface is weak, and this can result in irreversible ligand desorption from the NP surfaces due to the dynamic nature of coordination interactions. This can negatively affect the NP stability in biological media, in particular at low concentrations. Furthermore, ligands with weak affinity can be easily displaced by biomolecules bearing amine and carboxylic functional groups, which will eventually promote NP aggregation, making this strategy ineffective. See reference 22. Such problems should be overcome by developing multi-coordinating ligands, which improve the NP colloidal stability in biological media by enhancing the ligand affinity to the NP surfaces. See references 35 through 40. Our group has previously reported the design of multi-dopamine modified ligand consisting of a short poly(acrylic acid) (PAA) backbone laterally appended with a few catechol groups and several poly (ethylene glycol) (PEG) moieties via N,N'-dicyclohexylcarbodiimide (DCC) and N-(3-dimethylaminopropyl)-N'-ethylcarbodiimide (EDC) condensation. See reference 40. The resulting aqueous iron oxide (IO) nanoparticles (NP) were stable for one month in high acidic/basic conditions and at least 6 months in DI water. However, the use of polyacrylic acid (PAA) precursor for modification, where close proximity of the COOH groups along the backbone combined with the need to use DCC/EDC reagents, produced ligands with lower numbers of metal-coordinating groups (~6 dopamines per PAA chain); the PAA-based ligands also required thorough post-synthesis purification.

The present disclosure refers to the following references by number:
1. Lewin, M.; Carlesso, N.; Tung, C. H.; Tang, X. W.; Cory, D.; Scadden, D. T.; Weissleder, R., Tat peptide-derivatized magnetic nanoparticles allow in vivo tracking and recovery of progenitor cells. *Nat Biotechnol* 2000, 18 (4), 410-414.

2. Gupta, A. K.; Gupta, M., Synthesis and surface engineering of iron oxide nanoparticles for biomedical applications. *Biomaterials* 2005, 26 (18), 3995-4021.
3. Lee, J. H.; Huh, Y. M.; Jun, Y.; Seo, J.; Jang, J.; Song, H. T.; Kim, S.; Cho, E. J.; Yoon, H. G.; Suh, J. S.; Cheon, J., Artificially engineered magnetic nanoparticles for ultrasensitive molecular imaging. *Nature Medicine* 2007, 13 (1), 95-99.
4. Jun, Y. W.; Lee, J. H.; Cheon, J., Chemical design of nanoparticle probes for high-performance magnetic resonance imaging. *Angewandte Chemie-International Edition* 2008, 47 (28), 5122-5135.
5. Mattoussi, H.; Cheon, J., *Inorganic nanoprobes for biological sensing and imaging*. Artech House: Boston, 2009; 302 p.
6. Kim, J.; Piao, Y.; Hyeon, T., Multifunctional nanostructured materials for multimodal imaging, and simultaneous imaging and therapy. *Chem Soc Rev* 2009, 38 (2), 372-390.
7. Frey, N. A.; Peng, S.; Cheng, K.; Sun, S., Magnetic nanoparticles: synthesis, functionalization, and applications in bioimaging and magnetic energy storage. *Chem Soc Rev* 2009, 38 (9), 2532-2542.
8. Perez, J. M.; Josephson, L.; O'Loughlin, T.; Hogemann, D.; Weissleder, R., Magnetic relaxation switches capable of sensing molecular interactions. *Nat Biotechnol* 2002, 20 (8), 816-820.
9. Xu, C. J.; Xu, K. M.; Gu, H. W.; Zheng, R. K.; Liu, H.; Zhang, X. X.; Guo, Z. H.; Xu, B., Dopamine as a robust anchor to immobilize functional molecules on the iron oxide shell of magnetic nanoparticles. *J Am Chem Soc* 2004, 126 (32), 9938-9939.
10. Nasongkla, N.; Bey, E.; Ren, J. M.; Ai, H.; Khemtong, C.; Guthi, J. S.; Chin, S. F.; Sherry, A. D.; Boothman, D. A.; Gao, J. M., Multifunctional polymeric micelles as cancer-targeted, MRI-ultrasensitive drug delivery systems. *Nano Lett* 2006, 6 (11), 2427-2430.
11. Medarova, Z.; Pham, W.; Farrar, C.; Petkova, V.; Moore, A., In vivo imaging of siRNA delivery and silencing in tumors. *Nat Med* 2007, 13 (3), 372-377.
12. El-Boubbou, K.; Zhu, D. C.; Vasileiou, C.; Borhan, B.; Prosperi, D.; Li, W.; Huang, X. F., Magnetic Glyco-Nanoparticles: A Tool To Detect, Differentiate, and Unlock the Glyco-Codes of Cancer via Magnetic Resonance Imaging. *J Am Chem Soc* 2010, 132 (12), 4490-4499.
13. Santra, S.; Kaittanis, C.; Grimm, J.; Perez, J. M., Drug/Dye-Loaded, Multifunctional Iron Oxide Nanoparticles for Combined Targeted Cancer Therapy and Dual Optical/Magnetic Resonance Imaging. *Small* 2009, 5 (16), 1862-1868.
14. Rockenberger, J.; Scher, E. C.; Alivisatos, A. P., A new nonhydrolytic single-precursor approach to surfactant-capped nanocrystals of transition metal oxides. *J Am Chem Soc* 1999, 121 (49), 11595-11596.
15. Park, J.; An, K. J.; Hwang, Y. S.; Park, J. G.; Noh, H. J.; Kim, J. Y.; Park, J. H.; Hwang, N. M.; Hyeon, T., Ultra-large-scale syntheses of monodisperse nanocrystals. *Nature Materials* 2004, 3 (12), 891-895.
16. Sun, S. H.; Zeng, H.; Robinson, D. B.; Raoux, S.; Rice, P. M.; Wang, S. X.; Li, G. X., Monodisperse MFe2O4 (M=Fe, Co, Mn) nanoparticles. *J Am Chem Soc* 2004, 126 (1), 273-279.
17. Yu, W. W.; Falkner, J. C.; Yavuz, C. T.; Colvin, V. L., Synthesis of monodisperse iron oxide nanocrystals by thermal decomposition of iron carboxylate salts. *Chem Commun* 2004, (20), 2306-2307.
18. Jun, Y. W.; Huh, Y. M.; Choi, J. S.; Lee, J. H.; Song, H. T.; Kim, S.; Yoon, S.; Kim, K. S.; Shin, J. S.; Suh, J. S.; Cheon, J., Nanoscale size effect of magnetic nanocrystals and their utilization for cancer diagnosis via magnetic resonance imaging. *J Am Chem Soc* 2005, 127 (16), 5732-5733.
19. Zhang, F.; Lees, E.; Amin, F.; Gil, P. R.; Yang, F.; Mulvaney, P.; Parak, W. J., Polymer-Coated Nanoparticles: A Universal Tool for Biolabelling Experiments. *Small* 2011, 7 (22), 3113-3127.
20. Mattoussi, H.; Palui, G.; Na, H. B., Luminescent quantum dots as platforms for probing in vitro and in vivo biological processes. *Adv Drug Deliver Rev* 2012, 64 (2), 138-166.
21. Mout, R.; Moyano, D. F.; Rana, S.; Rotello, V. M., Surface functionalization of nanoparticles for nanomedicine. *Chem Soc Rev* 2012, 41 (7), 2539-2544.
22. Ling, D.; Hyeon, T., Chemical design of biocompatible iron oxide nanoparticles for medical applications. *Small* 2013, 9 (9-10), 1450-66.
23. Kim, B. S.; Qiu, J. M.; Wang, J. P.; Taton, T. A., Magnetomicelles: Composite nanostructures from magnetic nanoparticles and cross-linked amphiphilic block copolymers. *Nano Lett* 2005, 5 (10), 1987-1991.
24. Tromsdorf, U. I.; Bigall, N. C.; Kaul, M. G.; Bruns, O. T.; Nikolic, M. S.; Mollwitz, B.; Sperling, R. A.; Reimer, R.; Hohenberg, H.; Parak, W. J.; Forster, S.; Beisiegel, U.; Adam, G.; Weller, H., Size and surface effects on the MRI relaxivity of manganese ferrite nanoparticle contrast agents. *Nano Lett* 2007, 7 (8), 2422-2427.
25. Yu, W. W.; Chang, E.; Falkner, J. C.; Zhang, J. Y.; Al-Somali, A. M.; Sayes, C. M.; Johns, J.; Drezek, R.; Colvin, V. L., Forming biocompatible and nonaggregated nanocrystals in water using amphiphilic polymers. *J Am Chem Soc* 2007, 129 (10), 2871-2879.
26. Lin, C. A.; Sperling, R. A.; Li, J. K.; Yang, T. Y.; Li, P. Y.; Zanella, M.; Chang, W. H.; Parak, W. J., Design of an amphiphilic polymer for nanoparticle coating and functionalization. *Small* 2008, 4 (3), 334-341.
27. Pellegrino, T.; Manna, L.; Kudera, S.; Liedl, T.; Koktysh, D.; Rogach, A. L.; Keller, S.; Radler, J.; Natile, G.; Parak, W. J., Hydrophobic nanocrystals coated with an amphiphilic polymer shell: A general route to water soluble nanocrystals. *Nano Letters* 2004, 4 (4), 703-707.
28. Lees, E. E.; Nguyen, T. L.; Clayton, A. H. A.; Muir, B. W.; Mulvaney, P., The Preparation of Colloidally Stable, Water-Soluble, Biocompatible, Semiconductor Nanocrystals with a Small Hydrodynamic Diameter. *ACS nano* 2009, 3 (7), 1121-1128.
29. Wu, X. Y.; Liu, H. J.; Liu, J. Q.; Haley, K. N.; Treadway, J. A.; Larson, J. P.; Ge, N. F.; Peale, F.; Bruchez, M P, Immunofluorescent labeling of cancer marker Her2 and other cellular targets with semiconductor quantum dots. *Nat Biotechnol* 2003, 21 (4), 41-46.
30. Mikhaylov, G.; Mikac, U.; Magaeva, A. A.; Itin, V. I.; Naiden, E. P.; Psakhye, I.; Babes, L.; Reinheckel, T.; Peters, C.; Zeiser, R.; Bogyo, M.; Turk, V.; Psakhye, S. G.; Turk, B.; Vasiljeva, O., Ferri-liposomes as an MRI-visible drug-delivery system for targeting tumours and their microenvironment. *Nat Nanotechnol* 2011, 6 (9), 594-602.
31. Boyer, C.; Whittaker, M. R.; Bulmus, V.; Liu, J. Q.; Davis, T. P., The design and utility of polymer-stabilized iron-oxide nanoparticles for nanomedicine applications. *Npg Asia Mater* 2010, 2 (1), 23-30.
32. Xie, J.; Xu, C. J.; Xu, Z. C.; Hou, Y. L.; Young, K. L.; Wang, S. X.; Pourmond, N.; Sun, S. H., Linking hydrophilic macromolecules to monodisperse magnetite (Fe3O4) nanoparticles via trichloro-s-triazine. *Chem Mater* 2006, 18 (23), 5401-5403.

33. Amstad, E.; Gillich, T.; Bilecka, I.; Textor, M.; Reimhult, E., Ultrastable Iron Oxide Nanoparticle Colloidal Suspensions Using Dispersants with Catechol-Derived Anchor Groups. *Nano Letters* 2009, 9 (12), 4042-4048.

34. Wei, H.; Insin, N.; Lee, J.; Han, H. S.; Cordero, J. M.; Liu, W. H.; Bawendi, M. G., Compact Zwitterion-Coated Iron Oxide Nanoparticles for Biological Applications. *Nano Letters* 2012, 12 (1), 22-25.

35. Zhang, T. R.; Ge, J. P.; Hu, Y. X.; Yin, Y. D., A general approach for transferring hydrophobic nanocrystals into water. *Nano Lett* 2007, 7 (10), 3203-3207.

36. Shukoor, M. I.; Natalio, F.; Ksenofontov, V.; Tahir, M. N.; Eberhardt, M.; Theato, P.; Schroder, H. C.; Muller, W. E.; Tremel, W., Double-stranded RNA polyinosinic-polycytidylic acid immobilized onto gamma-Fe2O3 nanoparticles by using a multifunctional polymeric linker. *Small* 2007, 3 (8), 1374-8.

37. Liong, M.; Shao, H.; Haun, J. B.; Lee, H.; Weissleder, R., Carboxymethylated polyvinyl alcohol stabilizes doped ferrofluids for biological applications. *Adv Mater* 2010, 22 (45), 5168-72.

38. Stewart, M. H.; Susumu, K.; Mei, B. C.; Medintz, I. L.; Delehanty, J. B.; Blanco-Canosa, J. B.; Dawson, P. E.; Mattoussi, H., Multidentate Poly(ethylene glycol) Ligands Provide Colloidal Stability to Semiconductor and Metallic Nanocrystals in Extreme Conditions. *J Am Chem Soc* 2010, 132 (28), 9804-9813.

39. Ling, D.; Park, W.; Park, Y. I.; Lee, N.; Li, F.; Song, C.; Yang, S. G.; Choi, S. H.; Na, K.; Hyeon, T., Multiple-Interaction Ligands Inspired by Mussel Adhesive Protein: Synthesis of Highly Stable and Biocompatible Nanoparticles. *Angew Chem Int Edit* 2011, 50 (48), 11360-11365.

40. Na, H. B.; Palui, G.; Rosenberg, J. T.; Ji, X.; Grant, S. C.; Mattoussi, H., Multidentate catechol-based polyethylene glycol oligomers provide enhanced stability and biocompatibility to iron oxide nanoparticles. *ACS nano* 2012, 6 (1), 389-99.

41. Uyeda, H. T.; Medintz, I. L.; Jaiswal, J. K.; Simon, S. M.; Mattoussi, H., Synthesis of compact multidentate ligands to prepare stable hydrophilic quantum dot fluorophores. *J Am Chem Soc* 2005, 127 (11), 3870-3878.

42. Nikolic, M. S.; Krack, M.; Aleksandrovic, V.; Kornowski, A.; Forster, S.; Weller, H., Tailor-made ligands for biocompatible nanoparticles. *Angew Chem Int Edit* 2006, 45 (39), 6577-6580.

43. Pons, T.; Uyeda, H. T.; Medintz, I. L.; Mattoussi, H., Hydrodynamic dimensions, electrophoretic mobility, and stability of hydrophilic quantum dots. *Journal of Physical Chemistry B* 2006, 110 (41), 20308-20316.

44. Lee, N.; Hyeon, T., Designed synthesis of uniformly sized iron oxide nanoparticles for efficient magnetic resonance imaging contrast agents. *Chemical Society Reviews* 2012, 41 (7), 2575-2589.

45. Huang, J.; Bu, L. H.; Xie, J.; Chen, K.; Cheng, Z.; Li, X. G.; Chen, X. Y., Effects of Nanoparticle Size on Cellular Uptake and Liver MRI with Polyvinylpyrrolidone-Coated Iron Oxide Nanoparticles. *ACS nano* 2010, 4 (12), 7151-7160.

46. Xie, J.; Xu, C.; Kohler, N.; Hou, Y.; Sun, S., Controlled PEGylation of monodisperse $Fe_3O_4$ nanoparticles for reduced non-specific uptake by macrophage cells. *Advanced Materials* 2007, 19 (20), 3163-3166.

47. Mirkin, C. A.; Letsinger, R. L.; Mucic, R. C.; Storhoff, J. J., A DNA-based method for rationally assembling nanoparticles into macroscopic materials. *Nature* 1996, 382 (6592), 607-609.

48. Clapp, A. R.; Medintz, I. L.; Mauro, J. M.; Fisher, B. R.; Bawendi, M. G.; Mattoussi, H., Fluorescence resonance energy transfer between quantum dot donors and dye-labeled protein acceptors. *J Am Chem Soc* 2004, 126 (1), 301-310.

49. Mattoussi, H.; Mauro, J. M.; Goldman, E. R.; Anderson, G. P.; Sundar, V. C.; Mikulec, F. V.; Bawendi, M. G., Self-assembly of CdSe—ZnS quantum dot bioconjugates using an engineered recombinant protein. *J Am Chem Soc* 2000, 122 (49), 12142-12150.

50. Sapsford, K. E.; Algar, W. R.; Berti, L.; Gemmill, K. B.; Casey, B. J.; Oh, E.; Stewart, M. H.; Medintz, I. L., Functionalizing Nanoparticles with Biological Molecules: Developing Chemistries that Facilitate Nanotechnology. *Chemical Reviews* 2013, 113 (3), 1904-2074.

51. Guardia, P.; Di Corato, R.; Lartigue, L.; Wilhelm, C.; Espinosa, A.; Garcia-Hernandez, M.; Gazeau, F.; Manna, L.; Pellegrino, T., Water-Soluble Iron Oxide Nanocubes with High Values of Specific Absorption Rate for Cancer Cell Hyperthermia Treatment. *ACS nano* 2012, 6 (4), 3080-3091.

52. Piao, Y.; Jin, Z.; Lee, D.; Lee, H. J.; Na, H. B.; Hyeon, T.; Oh, M. K.; Kim, J.; Kim, H. S., Sensitive and high-fidelity electrochemical immunoassay using carbon nanotubes coated with enzymes and magnetic nanoparticles. *Biosensors & Bioelectronics* 2011, 26 (7), 3192-3199.

53. Jun, Y. W.; Seo, J. W.; Cheon, A., Nanoscaling laws of magnetic nanoparticles and their applicabilities in biomedical sciences. *Accounts Chem Res* 2008, 41 (2), 179-189.

54. Sandiford, L.; Phinikaridou, A.; Protti, A.; Meszaros, L. K.; Cui, X. J.; Yan, Y.; Frodsham, G.; Williamson, P. A.; Gaddum, N.; Botnar, R. M.; Blower, P. J.; Green, M. A.; de Rosales, R. T. M., Bisphosphonate-Anchored PEGylation and Radiolabeling of Superparamagnetic Iron Oxide: Long-Circulating Nanoparticles for in Vivo Multimodal (T1 MRI-SPECT) Imaging. *ACS Nano* 2013, 7 (1), 500-512.

55. Mattoussi, H.; Karasz, F. E.; Langley, K. H., Electrostatic and Screening Effects on the Dynamic Aspects of Polyelectrolyte Solutions. *J Chem Phys* 1990, 93 (5), 3593-3603.

56. Susumu, K.; Uyeda, H. T.; Medintz, I. L.; Pons, T.; Delehanty, J. B.; Mattoussi, H., Enhancing the stability and biological functionalities of quantum dots via compact multifunctional ligands. *J Am Chem Soc* 2007, 129 (45), 13987-13996.

57. Mei, B. C.; Susumu, K.; Medintz, I. L.; Delehanty, J. B.; Mountziaris, T. J.; Mattoussi, H., Modular poly(ethylene glycol) ligands for biocompatible semiconductor and gold nanocrystals with extended pH and ionic stability. *J Mater Chem* 2008, 18 (41), 4949-4958.

58. Susumu, K.; Mei, B. C.; Mattoussi, H., Multifunctional ligands based on dihydrolipoic acid and polyethylene glycol to promote biocompatibility of quantum dots. *Nat Protoc* 2009, 4 (3), 424-436.

59. Mei, B. C.; Susumu, K.; Medintz, I. L.; Mattoussi, H., Polyethylene glycol-based bidentate ligands to enhance quantum dot and gold nanoparticle stability in biological media. *Nat Protoc* 2009, 4 (3), 412-423.

SUMMARY OF THE INVENTION

The present invention is directed to a set of amphiphilic polymers. The amphipilic polymers may be suitable for use as ligands that can promote the dispersion of nanoparticles (NP), e.g., iron oxide (IO) nanoparticles (NP), in buffer media with great colloidal stability over a broad range of conditions. The ligands simultaneously present hydrophilic moieties, orthogonally reactive groups, and several anchoring groups. The polymer platform is synthesized using nucleophilic addition of several amine-presenting anchoring groups (e.g., dopamine) and hydrophilic and reactive moieties onto a poly(isobutylene-alt-maleic anhydride), PIMA, precursor. This ligand design greatly benefits from the high efficiency of the addition reaction, since maleic anhydride is highly reactive with any amine-presenting molecule. Furthermore, this reaction can be carried out without the need for additional reagents or excess reactants, while allowing simultaneous coupling of all desired groups in one step.

These polymer ligands have provided a set of compact hydrophilic iron oxide NPs that exhibited excellent colloidal stability over a broad pH range and in the presence of excess electrolytes over at least 1 year. Dynamic light scattering measurements confirmed the colloidal stability and relative compactness of the resulting NPs. We also conjugated Cy3 dye to amine-functionalized NPs yielding a dual-mode optical-MRI platform, which was used for cell imaging with good bio-distribution. Viability assays using MTT (3-(4,5-dimethylthiazol-2-yl)-2,5-diphenyltetrazolium bromide) showed that the hydrophilic NPs exhibit no measurable toxicity to live cells. Additional MRI relaxometry experiments showed that these NPs exhibit size- and concentration-dependent $T_2$ relaxation effect, with large size-dependent $r_2$ relaxivity values.

The present invention is therefore directed to a composition comprising a polymer comprising a repeat unit (A) having the following structure:

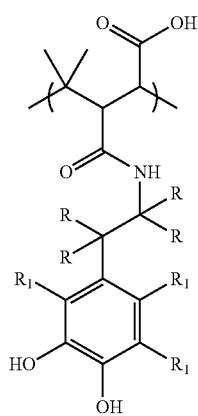

(A)

wherein each R is independently —H or —COOH, and each $R_1$ is independently —H, —NO$_2$, or —OH.

The present invention is further directed to a composition comprising a polymer, the polymer prepared by reacting poly(isobutylene-alt-maleic anhydride) having the following general structure:

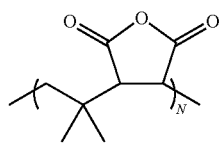

poly(isobutylene-alt-maleic anhydride)

wherein N has a value between about 10 and about 20,000; with an amine-containing reactant having the following structure:

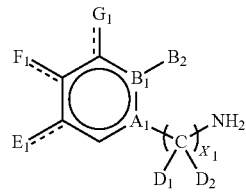

wherein $A_1$ is N or C;
$B_1$ is C, N, or O;
$B_2$ is —H, —CH$_3$, or —NO$_2$;
Each $D_1$ and $D_2$ are independently —H or —COOH;
Each $E_1$, $F_1$, and $G_1$ are independently —OH, —H, or =O; and
$X_1$ is 1 or 2.

The present invention is still further directed to a method of preparing a polymer comprising repeat unit (A):

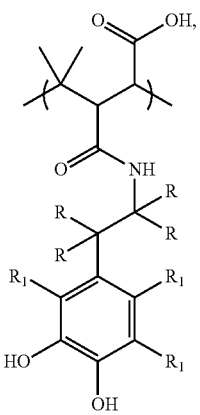

(A)

the method comprising contacting poly(isobutylene-alt-maleic anhydride) with an amine-containing reactant having the general structure:

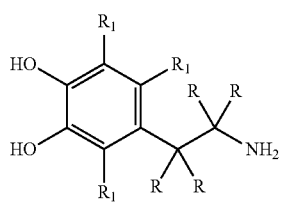

wherein each R is independently hydrogen or —COOH, and
each $R_1$ is independently —H, —NO$_2$, or —OH.

Other objects and features will be in part apparent and in part pointed out hereinafter.

BRIEF DESCRIPTION OF THE DRAWINGS

FIGS. 6A through 6G are images of a representative set of fluorescence images collected from HeLa cells incubated with 4'-6-diamidino-2-phenylindole (DAPI), the $Fe_3O_4$-Cy3 conjugates, and transferrin-Cy5. The images are confocal laser scanning microscopy images of HeLa cells incubated with $Fe_3O_4$-Cy3 for 1 hour. FIG. 6A depicts nuclei stained with blue 4'-6-diamidino-2-phenylindole (DAPI). FIG. 6B depicts spot-like yellow fluorescence showing internalized $Fe_3O_4$-Cy3. FIG. 6C depicts a merged image of blue (DAPI) and yellow ($Fe_3O_4$-Cy3) signals. Scale bar=20 μm. FIGS. 6D through 6G are confocal laser scanning microscopy images of HeLa cells incubated with $Fe_3O_4$-Cy3 conjugates and transferrin-Cy5 (as endosome-specific marker) for 1 h. The distribution of patterns containing $Fe_3O_4$-Cy3 (yellow, FIG. 6E) was co-localized with those of the Cy5-transferrin (red, FIG. 6F). Scale bar=20 μm.

DESCRIPTION OF THE EMBODIMENT(S) OF THE INVENTION

Figure 1:
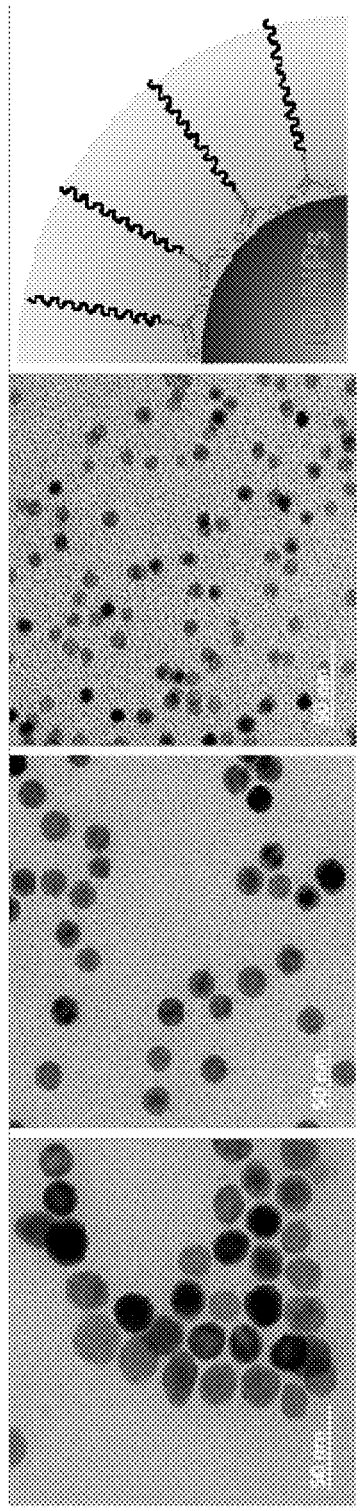
FIGS. 1A, 1B, and 1C are TEM images of iron oxide nanoparticles with 10.5 nm (FIG. 1A), 8.0 nm (FIG. 1B) and 4.6 nm (FIG. 1C) core radius before ligand exchange.
FIG. 1D is a depiction of the iron oxide particles comprising the oleate capping groups.

One aspect of the invention is a multifunctional and multicoordinating polymer ligand. The polymer ligand is optimally suited for surface-functionalizing nanoparticles (NPs), e.g., iron oxide and potentially other magnetic nanoparticles (NPs). The ligand is capable of promoting the integration of the surface functionalized nanoparticle into biological systems. In some embodiments, an amphiphilic polymer according to the present invention is prepared by coupling (via nucleophilic addition) an amine-containing reactant comprising an anchoring group (e.g., but not limited to, dopamine) onto a poly(isobutylene-alt-maleic anhydride) (PIMA) chain. In some embodiments, an amphiphilic polymer according to the present invention is prepared by coupling (via nucleophilic addition) an amine-containing reactant comprising an anchoring group (e.g., but not limited to, dopamine) and a polyethylene glycol reactant onto a poly(isobutylene-alt-maleic anhydride) (PIMA) chain. This design greatly benefits from the highly-efficient and reagent-free one-step reaction of maleic anhydride groups with amine-containing molecules. In some preferred embodiments, the availability of several dopamine groups in the same ligand greatly enhances the ligand affinity, via multiple-coordination, to nanoparticles, e.g., magnetic NPs, while the hydrophilic and reactive groups promote colloidal stability in buffer media and allow subsequent conjugation with target biomolecules. Iron oxide (IO) nanoparticles (NP) ligand-exchanged with these polymer ligands have compact hydrodynamic size and exhibit enhanced long-term colloidal stability over the pH range 4-12 and in presence of excess electrolytes. Nanoparticles ligated with terminally reactive polymers have been easily coupled to target dyes and tested in live cell imaging with no measurable cytotoxicity. Finally, the resulting hydrophilic nanoparticles exhibit large and size-dependent $r_2$ relaxivity values.

I. Ligand Design

The polymer ligands developed in this study to promote the transfer of nanoparticles, e.g., iron oxide (IO) nanoparticles (NP), from hydrophobic to aqueous media while conferring on them biocompatibility, take advantage of a few unique features of poly(isobutylene-alt-maleic anhydride) (PIMA). One of them is the efficiency of the addition reaction between anhydride rings and amine groups. Indeed, maleic anhydride is highly reactive, via nucleophilic addition, with any amine-presenting molecule. This coupling reaction can be carried out in organic media and without the need of additional reagents, which simplifies the purification steps and the ensuing characterization of the prepared materials. Furthermore, the availability of several maleic anhydride rings per polymer chain allows the grafting of multiple lateral groups with distinct chemical functionalities. In particular, it permits a straightforward and controlled insertion of several coordinating groups in the same polymer, which enhances the ligand-to-nanocrystal binding affinity. See reference 20. It can also allow the introduction of highly biocompatible moieties (e.g., short PEG chains or zwitterion groups) and reactive functional groups (e.g., but not limited to, amine, azide, or thiol), which will allow further coupling to target molecules while drastically reducing non-specific interactions. We should also note that poly(isobutylene-alt-maleic anhydride) being a copolymer (where anhydride rings alternate with the dimethylpropane groups) along the chain presents a few chemical advantages. For example, the presence of dimethyl groups between adjacent anhydride rings reduces steric constraints and enhances their reactivity, allowing high degrees of substitutions during the addition reaction. Thus, larger numbers of anchoring groups and hydrophilic/reactive moieties can be introduced in the amphiphilic ligand. This constitutes a substantial improvement over the Oligo-PEG-Dopa ligand design reported in our previous study. See reference 40. Though a smaller molecular weight PAA polymer was used in that study, we found that the close proximity of the carboxy groups, combined with the need to use N,N'-dicyclohexylcarbodiimide (DCC)/N-(3-dimethylaminopropyl)-N'-ethylcarbodiimide (EDC) condensation reaction to graft dopamines and PEGs onto the PAA backbone, did not allow the insertion of high numbers of anchoring groups; less than 6 dopamine groups per polymer ligands were introduced. See reference 40. In addition, because (DCC)/(EDC) coupling reaction generates rather large amounts of side products (e.g., urea) along with unreacted precursors, additional purification steps were required to isolate the final product. Such constraints are also encountered with other polymer designs for either ligand exchange or encapsulation. See references 25 and 40. The present PIMA precursor addresses most of those issues. We should also stress that the present ligand design (and the surface functionalization strategy as a whole) is drastically different from the one relying on encapsulation within amphiphilic block-copolymer described in previous studies, albeit both routes start with similar PIMA precursors. See references 25 through 27. Our approach requires the removal of the native cap since the metal chelating groups must interact directly with the nanoparticle surface. We were able to introduce a larger variety of PEG and amine containing moieties (e.g., but not limited to, dopamine) in the same polymer ligand. Furthermore, this ligand design provided $Fe_3O_4$ nanoparticles with smaller hydrodynamic size and substantially improved colloidal stability, while allowing surface reactivity (see below). This produces a two-dimensional dense polymer coating layer on the NPs, a result that reflects the strong coordination onto the metal-rich surface and the use of rather small size PEG chains in this design.

The poly(isobutylene-alt-maleic anhydride) (PIMA) platform may comprise between about 10 and about 40,000 repeat units. In general, commercially available PIMA has a number of repeat units between about 10 and about 20,000, such as between about 10 and about 10,000, or between about 10 and about 5,000. In general, commercially available PIMA has a number of repeat units between about 10 repeat units and about 2000 repeat units, such as between about 20 repeat units and about 1000 repeat units, between about 20 repeat units and about 400 repeat units, such as between about 20 repeat units and about 100 repeat units, such as between about 30 repeat units and about 50 repeat units, or between about 35 repeat units and about 45 repeat units, such as about 39 repeat units. The molecular weight of the PIMA platform may be between about 150 Daltons and about 2,000,000 Daltons, such as between about 300 Daltons and about 800,000 Daltons, or between about 300 Daltons and about 200,000 Daltons, or between about 4500 Daltons and about 70,000 Daltons. A commercially available PIMA has an average Mw of about 165,000 Daltons. Another commercially available PIMA has an average Mw of about 60,000 Daltons. Another commercially available PIMA has an average Mw of about 6000 Daltons. In some embodiments, a commercially-available PIMA having Mw~6 kDa was suitable. See reference 26. The maleic anhydride rings were either fully or partially reacted to provide controlled numbers of side groups bound to the backbone via an amide bond; it also frees several carboxylic groups (as many as the number of maleic anhydride rings present), which can provide additional hydrophilic and potential reactive groups in the final compound. We anticipate that for the molecular weight of approximately 6000 Daltons of polymer reported by the manufacturer the average number of monomers per PIMA chain (or index of polymerization) is equal to 39; a mass for the monomer unit of ~154 g/mol was used. During synthesis, we adjusted the molar amount of each amine-containing moiety with respect to the overall molar amount of monomer units in the precursor polymer. As will be shown more fully below, three sets of dopamine-modified ligands may be identified as follows: Dopa-PIMA (compound 1), Dopa-PIMA-PEG (compound 2) and multi-reactive Dopa-PIMA-PEG-R (compound 3) where R designates a laterally reactive group.

Overall this chemical design offers a few clear advantages: 1) The highly reactive maleic anhydride rings combined with the copolymer nature of the precursor allow effective coupling between PIMA and a variety of amine-presenting molecules. This permits one to introduce (in one step reaction) large but controlled numbers of anchoring, hydrophilic and reactive functions, all in the same structures. 2) No additional reagents (e.g. DCC or EDC) are needed to facilitate the coupling; this also eliminates problems associated with ligand purification. See reference 40. 3) This design can potentially be expanded to prepare additional platforms that are optimized for other nanoparticles including QDs and metal nanoparticles.

II. Synthesis and Characterization

In some embodiments, the polymer of the present invention is synthesized using poly(isobutylene-alt-maleic anhydride) as a starting reactant and platform. Poly(isobutylene-alt-maleic anhydride) (referred to as PIMA throughout this specification) has the following general structure:

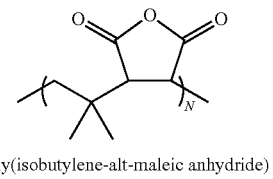

poly(isobutylene-alt-maleic anhydride)

wherein N has a value between about 10 and about 40,000, such as between about 10 and about 20,000, such as between about 10 and about 10,000, or between about 10 and about 5,000. In general, commercially available PIMA has a number of repeat units between about 10 repeat units and about 2000 repeat units, such as between about 20 repeat units and about 1000 repeat units, between about 20 repeat units and about 400 repeat units, such as between about 20 repeat units and about 100 repeat units, such as between about 30 repeat units and about 50 repeat units, or between about 35 repeat units and about 45 repeat units, such as about 39 repeat units. The molecular weight of the PIMA platform may be between about 150 Daltons and about 2,000,000 Daltons, such as between about 300 Daltons and about 800,000 Daltons, or between about 300 Daltons and about 200,000 Daltons, or between about 4500 Daltons and about 70,000 Daltons. A commercially available PIMA has an average Mw of about 165,000 Daltons. Another commercially available PIMA has an average Mw of about 60,000 Daltons. Another commercially available PIMA has an average Mw of about 6000 Daltons.

According to the present invention, PIMA may be contacted with a reactant comprising a primary and/or secondary amine for nucleophilic coupling to maleic anhydride and an aromatic ring comprising at least two hydroxyl groups and/or at least one hydroxyl and at least one carbonyl on adjacent carbons in the ring, e.g., a catechol ring, which may be substituted or unsubstituted.

In some embodiments, PIMA may be contacted with an amine-containing reactant having the general structure:

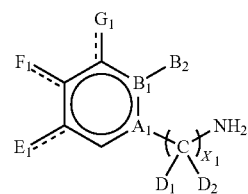

wherein $A_1$ is N or C;
$B_1$ is C, N, or O;
$B_2$ is —H, —$CH_3$, or —$NO_2$;
Each $D_1$ and $D_2$ are independently —H or —COOH;

Each $E_1$, $F_1$, and $G_1$ are independently —OH, —H, or =O; and $X_1$ is 1 or 2.

In some embodiments, the bonds to $E_1$, $F_1$, and $G_1$ may be single bonds or double bond. In some embodiments, preferably the amine-containing reactant comprises no more than one $D_1$ or $D_2$ comprising —COOH. In some embodiments, at least two of $E_1$, $F_1$, and $G_1$ are —OH.

In some embodiments, the polymer may have the following repeat unit (H):

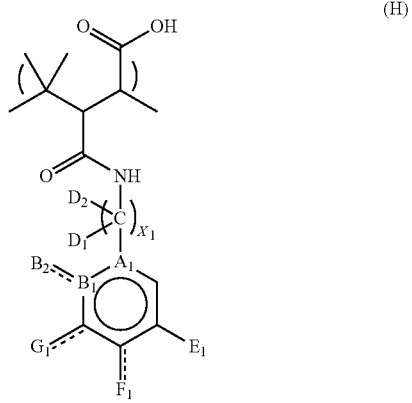

(H)

wherein $A_1$ is N or C;
$B_1$ is C, N, or O;
$B_2$ is —H, —CH$_3$, or —NO$_2$;
Each $D_1$ and $D_2$ are independently —H or —COOH;
Each $E_1$, $F_1$, and $G_1$ are independently —OH, —H, or =O; and
$X_1$ is 1 or 2.

In some embodiments, the bonds to $E_1$, $F_1$, and $G_1$ may be single bonds or double bond. In some embodiments, preferably the amine-containing reactant comprises no more than one $D_1$ or $D_2$ comprising —COOH. In some embodiments, at least two of $E_1$, $F_1$, and $G_1$ are —OH. In some embodiments, at least two adjacent $E_1$, $F_1$, and $G_1$ are —OH.

In some embodiments, PIMA may be contacted with an amine-containing reactant selected from among dopamine; 2-amino-3-(3,4-dihydroxyphenyl)propanoic acid; L-DOPA (L-3,4-dihydroxyphenylalanine, (S)-2-amino-3-(3,4-dihydroxyphenyl)propanoic acid); D-DOPA (L-3,4-dihydroxyphenylalanine, (S)-2-amino-3-(3,4-dihydroxyphenyl)propanoic acid); norepinephrine; epinephrine; 2-amino-3-(4,5-dihydroxy-2-nitrophenyl)propanoic acid; 6-nitrodopamine (4-(2-aminoethyl)-5-nitrobenzene-1,2-diol); 5-hydroxydopamine (5-(2-aminoethyl)benzene-1,2,3-triol); 2-amino-3-(3,4-dihydroxypyridin-1(4H)-yl)propanoic acid; 2-amino-3-(3-hydroxy-4-oxopyridin-1(4H)-yl)propanoic acid; 1-(2-aminoethyl)-3-hydroxy-2-methylpyridin-4(1H)-one; 2-(aminomethyl)-5-hydroxy-4H-pyran-4-one; and the like.

In some embodiments, PIMA may be contacted with an amine-containing reactant having the general structure:

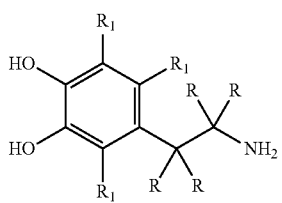

wherein each R is independently hydrogen or —COOH, and
each $R_1$ is independently —H, —NO$_2$, or —OH.

In some embodiments, preferably the amine-containing reactant comprises no more than one R comprising —COOH. Stated another way, three or more R are hydrogen. In some embodiments, each $R_1$ comprises —H.

In some preferred embodiments, PIMA may be contacted with dopamine, which has the following structure:

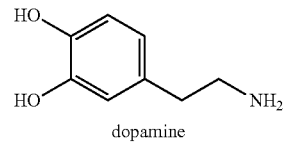 [SMILES: NCCc1ccc(O)c(O)c1]

dopamine

Contact with the amine-containing reactant causes a ring-opening reaction to occur in which the amine-containing reactant is coupled to the maleic anhydride moiety using nucleophilic addition. The contact may occur in an organic, aprotic solvent, such as dimethylformamide, hexane, benzene, toluene, 1,4-dioxane, chloroform, diethyl ether, dichloromethane, tetrahydrofuran, ethyl acetate, acetone, acetonitrile, dimethylsulfoxide, and the like. In general, the nucleophilic coupling reaction may occur at elevated temperatures, such as between about 25° C. and about 200° C., such as between about 35° C. and about 100° C., such as between about 40° C. and about 70° C.

In some embodiments, reaction between PIMA and an amine-containing reactant having the general structure:

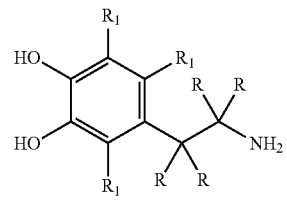

yields polymer comprising the repeat unit (A) having the structure shown below:

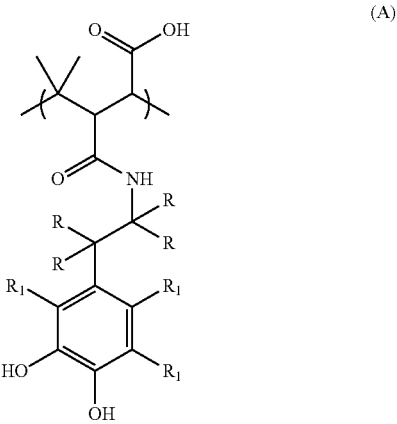

(A)

wherein each R is independently hydrogen or —COOH, and
each $R_1$ is independently —H, —NO$_2$, or —OH.

In some preferred embodiments, PIMA may be contacted with dopamine. In some embodiments, reaction between PIMA and dopamine yields polymer comprising the repeat unit (B) having the structure shown below:

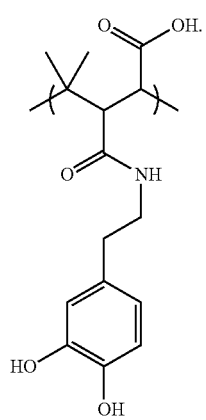

(B)

The reaction mixture may comprise PIMA and amine-containing reactant in relative amounts sufficient to react between about 2% and about 100%, between about 10% and about 100%, between about 20% and about 80%, or between about 30% and about 70% of the maleic anhydride units along the PIMA platform. Maleic anhydride ring opening may yield an unreacted carboxyl group, which may remain unreacted or may be coupled with additional moieties. Additionally, maleic anhydride that is not coupled with amine-containing reactant may nonetheless undergo ring opening. In some embodiments, therefore, the polymer may additionally comprise a repeat unit that results from ring opening, but not coupling with an amine-containing reactant. In some embodiments, the polymer may comprise a repeat unit (C), having the structure shown below:

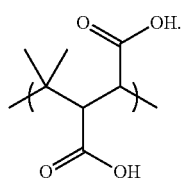

(C)

In some embodiments, the composition comprising the polymer comprising repeat units (B) and (C) may have the following structure, referred to herein as Compound 1:

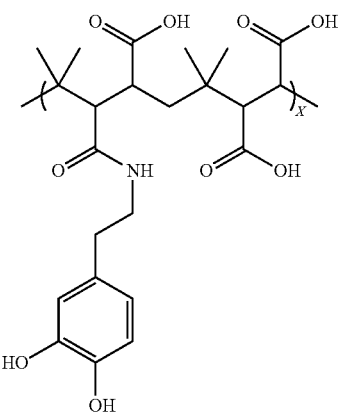

Compound 1 wherein X has a value between about 10 and about 40,000, such as between about 10 and about 20,000, such as between about 10 and about 10,000, or between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units Compound 1 is referred to herein as Dopa-PIMA.

In some embodiments, the reaction may incorporate a polyethylene glycol reactant comprising an amine group and a terminal functional group. The synthesis of amine-terminated inert and reactive poly(ethylene glycol) reactant is provided in the examples. In general, a structure of a poly(ethylene glycol) reactant may be as follows:

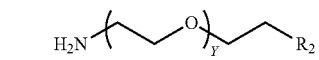

wherein Y has a value between one and about 100 and each $R_2$ is independently selected from the group consisting of hydroxy (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12 or about 15.

The coupling reaction between a poly(ethylene glycol) reactant and the maleic anhydride moiety of PIMA yields polymer comprising repeat unit (D):

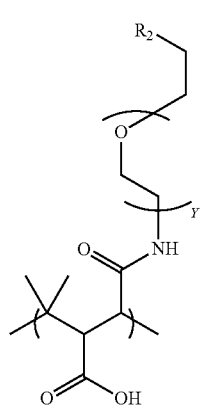

(D)

wherein Y has a value between one and about 100 and each R is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12 or about 15.

Incorporation of a poly(ethylene glycol) reactant into the reaction mixture comprising PIMA and the amine-containing reactant may yield a polymer having multiple repeat units selected from among (B), (C), and (D) as provided above. In some embodiments, the reaction mixture may comprise PIMA, amine-containing reactant, and poly(ethylene glycol) reactant in relative amounts sufficient to react between about 2% and about 100%, between about 10% and about 100%, between about 20% and about 80%, or between about 30% and about 70% of the maleic anhydride units. The molar ratio of amine-containing reactant and poly(ethylene glycol) reactant may be between about 4:1 to about 1:4, such as between about 3:1 to about 1:3, such as between about 2:1 to about 1:2, such as about 1:1.

In some embodiments, the polymer of the present invention may have the structure:

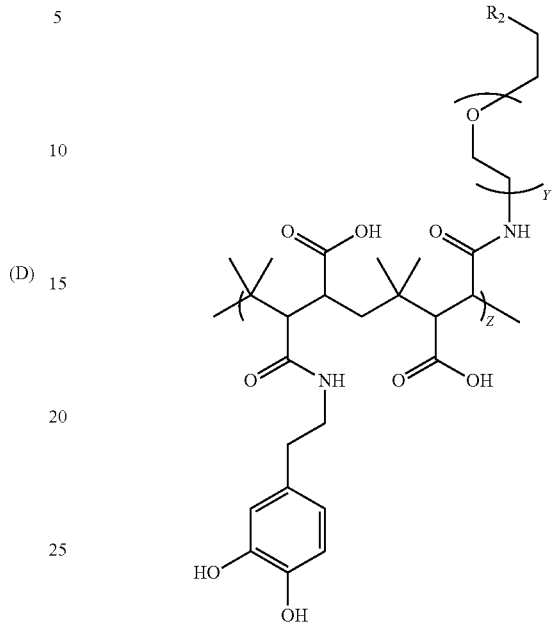

wherein Y has a value between one and about 100, Z has a value between about 10 and about 10,000, and each R$_2$ is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin. In some embodiments, Y may have a value between 5 and about 50, such as between 10 and about 20, such as about 12 or about 15. In some embodiments, Z may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments of the invention, the R$_2$ group may be functionalized with an amine-reactive fluorescent dye in order to couple the dye to the polymer. Exemplary dyes for coupling to the polymer include Cyanine3 NHS ester, Cyanine5 NHS ester, Cyanine3.5 NHS ester, Cyanine5.5 NHS ester, Alexa Fluor® 488 NHS Ester, and X-Rhodamine-5-(and -6)-Isothiocyanate (5(6)-XRITC).

In some embodiments, the amine-terminated inert and reactive poly(ethylene glycol) precursor may be capped with methoxy. For example, the PEG precursor may have the structure:

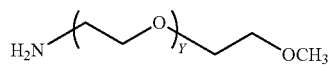

wherein Y has a value between one and about 100. In some embodiments, Y may have a value between 5 and about 50, such as between 10 and about 20, such as about 12 or about 15.

Coupling a PEG precursor capped with methoxy with PIMA may yield a polymer comprising the following repeat unit (E):

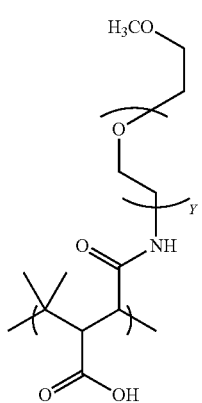

(E)

wherein Y has a value between one and about 100. In some embodiments, Y may have a value between 5 and about 50, such as between 10 and about 20, such as about 12 or about 15.

In some embodiments, the reaction mixture may comprise PIMA, dopamine, and a PEG precursor capped with methoxy. Such reaction may yield a polymer having the structure:

Compound 2

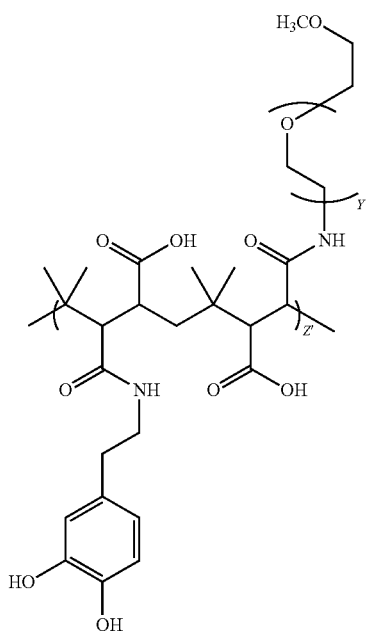

wherein Y has a value between one and about 100 and Z' has a value between about 10 and about 10,000. Herein, this polymer may be referred to as Compound 2. In some embodiments, Y may have a value between 5 and about 50, such as between 10 and about 20, such as about 12. In some embodiments, Z' may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units. In some embodiments, the reaction mixture may comprise PIMA, amine-containing reactant, and poly(ethylene glycol) reactant in relative amounts sufficient to react between about 2% and about 100%, between about 10% and about 100%, between about 20% and about 80%, or between about 30% and about 70% of the maleic anhydride units. The molar ratio of amine-containing reactant and poly(ethylene glycol) reactant may be between about 4:1 to about 1:4, such as between about 3:1 to about 1:3, such as between about 2:1 to about 1:2, such as about 1:1.

In some embodiments, the amine-terminated inert and reactive poly(ethylene glycol) precursor may be capped with azide. For example, the PEG precursor may have the structure:

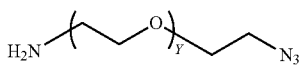

wherein Y has a value between one and about 100. In some embodiments, Y may have a value between 5 and about 50, such as between 10 and about 20, such as about 12 or about 15.

Coupling a PEG precursor capped with azide with PIMA may yield a polymer comprising the following repeat unit (F):

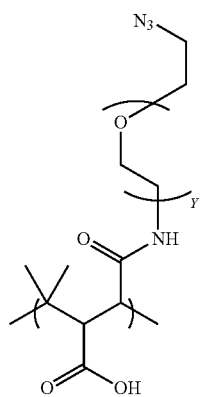

(F)

wherein Y has a value between one and about 100. In some embodiments, Y may have a value between 5 and about 50, such as between 10 and about 20, such as about 12 or about 15.

In some embodiments, the reaction mixture may comprise PIMA, dopamine, and a PEG precursor capped with azide. Such reaction may yield a polymer having the structure:

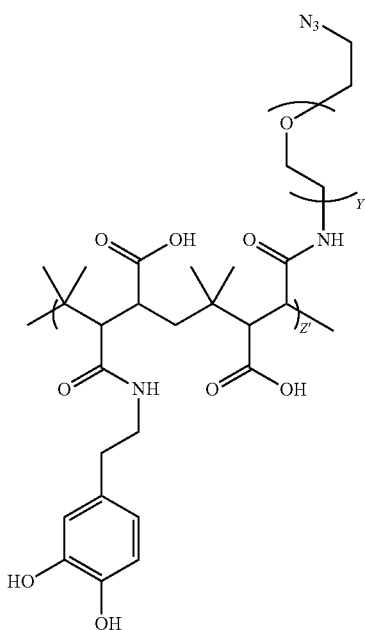

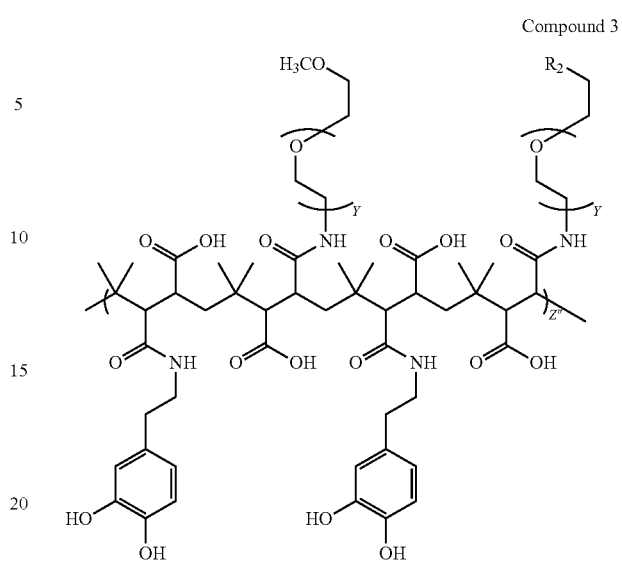

Compound 3 wherein Y has a value between one and about 100 and Z' has a value between about 10 and about 10,000. In some embodiments, Y may have a value between 5 and about 50, such as between 10 and about 20, such as about 12 or about 15. In some embodiments, Z' may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units. In some embodiments, the reaction mixture may comprise PIMA, amine-containing reactant, and poly(ethylene glycol) reactant in relative amounts sufficient to react between about 2% and about 100%, between about 10% and about 100%, between about 20% and about 80%, or between about 30% and about 70% of the maleic anhydride units. The molar ratio of amine-containing reactant and poly(ethylene glycol) reactant may be between about 4:1 to about 1:4, such as between about 3:1 to about 1:3, such as between about 2:1 to about 1:2, such as about 1:1.

wherein each Y independently has a value between one and about 100, each $R_2$ is independently selected from the group consisting of hydroxyl (—OH), methoxy (—OCH$_3$), amino (—NH$_2$), azido (—N$_3$), thiol (—SH), lipoic acid, ethynyl (—C≡CH), carboxyl (—COOH), aldehyde (—C(O)H), maleimide, and biotin, and Z" has a value between about 10 and about 10,000. In some embodiments, Y may have a value between 5 and about 50, such as between 10 and about 20, such as about 12 or about 15. In some embodiments, Z" may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units. In some embodiments, the reaction mixture may comprise PIMA, amine-containing reactant, and poly (ethylene glycol) reactant in relative amounts sufficient to react between about 2% and about 100%, between about 10% and about 100%, between about 20% and about 80%, or between about 30% and about 70% of the maleic anhydride units. The molar ratio of amine-containing reactant and poly(ethylene glycol) reactant may be between about 4:1 to about 1:4, such as between about 3:1 to about 1:3, such as between about 2:1 to about 1:2, such as about 1:1. Moreover, the molar ratio of the two poly(ethylene glycol) reactants may be between about 4:1 to about 1:4, such as between about 3:1 to about 1:3, such as between about 2:1 to about 1:2, such as about 1:1.

In order to prepare the polymer referred to herein as Compound 3, the reaction mixture may comprise PIMA, dopamine, a PEG precursor capped with methoxy, and a PEG precursor capped with another functional group. An exemplary structure of Compound 3 is provided below:

In some embodiments, the reaction mixture may comprise PIMA, dopamine, a PEG precursor capped with methoxy, and a PEG precursor capped with azide. In some embodiments, the polymer may comprise repeat units (B), (C), (E), and (F). In some embodiments, the polymer of the present invention may comprise the following repeat units:

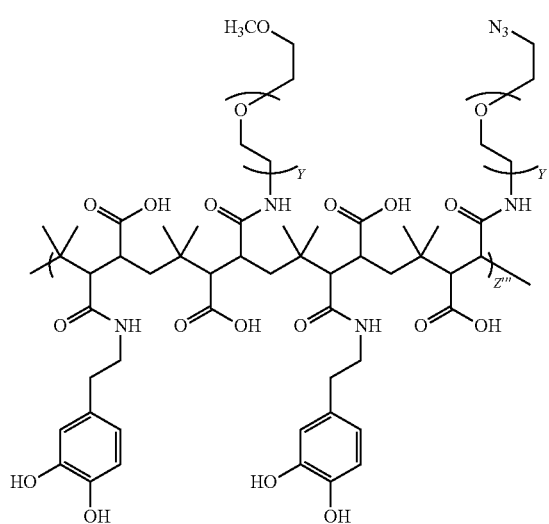

wherein each Y independently has a value between one and about 100 and Z'" has a value between about 10 and about 10,000. In some embodiments, Y may have a value between 5 and about 50, such as between 10 and about 20, such as about 12 or about 15. In some embodiments, Z'" may have a value between about 10 and about 5,000, or between about 10 repeat units and about 2000 repeat units, such as between about 20 repeat units and about 1000 repeat units, between about 20 repeat units and about 400 repeat units, such as between about 20 repeat units and about 100 repeat units.

In some embodiments, the reaction mixture may comprise PIMA, dopamine, and N-(2-aminoethyl)-4-(1,2-dithiolan-3-yl)butamide (amine terminated lipoic acid). Such a reaction mixture may yield a polymer comprising repeat units (B), (C), and (G), which is represented below:

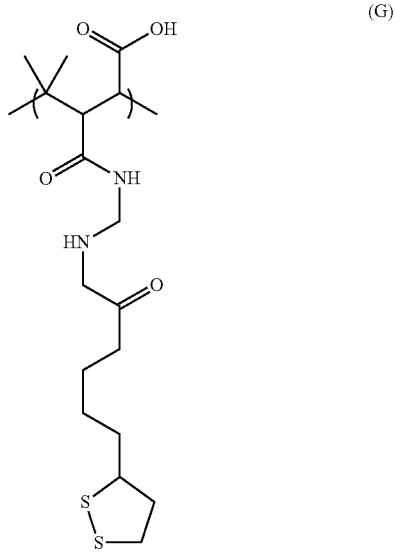

(G)

Polymers of the present invention may comprise repeat units (A), (B), (C), (D), (E), (F), (G), and (H) in any combination and any arrangement. The repeat units may be arranged in random, alternating, or block formations.

A polymer according to the present invention may have a molecular weight, Mw, between about 1000 Daltons and about 1,000,000 Daltons, such as between about 1000 Daltons and about 500,000 Daltons. In some embodiments, the polymer may comprise between about 10 repeat units and about 20,000 repeat units, such as between about 10 repeat units and about 10,000 repeat units, such as between about 10 repeat units and about 1000 repeat units, or between about 10 repeat units and about 100 repeat units, or between about 20 repeat units and about 50 repeat units.

1) Dopa-PIMA (compound 1) is the simplest one and involved reacting activated dopamine with PIMA. In some embodiments, 50% of the maleic anhydride rings (~20 units) in the polymer chain were targeted for reaction with dopamine, leaving the other 50% intact. The use of only 50% mole fraction of dopamine allows a side-by-side comparison with the other PEGylated ligands (e.g., Dopa-PIMA-PEG) by providing the same number of dopamine groups per polymer platform during ligand exchange and the subsequent analysis. 2) The second set is Dopa-PIMA-PEG (compound 2), which presents several PEG moieties and dopamine groups in the same platform. Typically, a total molar amount of aminated molecules equal to the molar concentration of maleic anhydride groups is used, with a 50:50 mixture of dopamine and $H_2N$-PEG-OMe. This is expected to introduce a total of ~39 dopamines and PEG moieties, while freeing ~39 carboxy groups along the polymer chain, which ensures that there are enough anchoring groups for effective coordination onto the NP surface and PEG segments for enhanced affinity to buffer media. See references 26, 39, 41, and 42. 3) The third set of ligands, Dopa-PIMA-PEG-R (compound 3), contains a stoichiometric mixture of dopamine, methoxy-PEG and reactive-PEG groups. This was achieved by replacing a fraction of the amine-PEG-OCH$_3$ with amine-PEG-R during the addition reaction. For instance, substituting 10-30% of $H_2N$-PEG-OMe (used to prepare compound 2) with $H_2N$-PEG-R during the substitution/addition reaction, a set of reactive polymer ligands, Dopa-PIMA-PEG-R, with ~4 to 12 reactive functions can be prepared. We should note that the nucleophilic addition reaction between the maleic anhydride and aminated-PEG and dopamine could be completed within a few hours (4-8 hours), though overnight reactions were used in the present study.

To address the poor reactivity of dopamine hydrochloride the salt was first activated by adding an equimolar amount of triethylamine in dry DMF for 2 hours followed by centrifugation to remove insoluble salt (e.g., triethylamine hydrochloride). Carrying out the activation and addition reaction in subsequent steps is more effective than simply mixing the dopamine hydrochloride and triethylamine with the PIMA in the same solution. This improves the overall yield of the coupling reaction. Indeed, we found that when preparing Dopa-PIMA ligand, the starting PIMA solution was slightly cloudy but gradually became homogeneous and colorless after ~1 hour of the addition of activated dopamine.

Finally we should note that the physical state of the three ligands after purification is influenced by the nature of the substituted groups. While a white powder was collected for the purified Dopa-PIMA ligand, a viscous yellowish oil material was collected for the PEG-containing ligand. The final yield of the addition reaction was slightly higher for compound 1, with 91% yield measured for compound 1 and about 76% for compounds 2 and compound 3.

The ligands were characterized using $^1$H NMR spectroscopy. The $^1$H NMR spectra for all three ligands (in DMSO-$d_6$) show a multiplet peak at 6.4-6.7 ppm (attributed to the aromatic protons from catechol). They also show a broad peak around 0.9 ppm ascribed to protons of methyl groups in the polymer. The stoichiometry of the ligands for each compound was estimated from the corresponding $^1$H NMR spectrum by comparing the relative integrations of the hydrogen peaks from the two methyl groups in the repeat units ($\delta$~0.9 ppm, 234 H) and the three aromatic protons per catechol ($\delta$=6.4-6.7 ppm). From the integration, we measured ~19 dopamines (57.72 H) per ligand for compound 1, a value consistent with the total number of maleic anhydride rings in the PIMA precursor and the fact that only 50% mole fraction of those were targeted for coupling. For compound 2 (Dopa-PIMA-PEG), the $^1$H NMR spectrum showed a strong peak at 3.5 ppm (emanating from the PEG moieties) and a sharp peak at 3.23 ppm (from the methoxy groups), in addition to the multiplet at 6.4-6.7 ppm. Analysis of the integration of the above NMR peaks in the Dopa-PIMA-PEG spectrum provided estimates for the number of dopamine and PEG moieties grafted along the PIMA backbone. We measured an average of ~19 dopamine groups (56.56 H) and ~20 PEG-OMe moieties (61.52 H) per polymer chain. Overall, the above analysis indicate that the coupling efficiency between maleic anhydride and amino-containing molecules (here dopamine and H$_2$N-PEG-OMe) is essentially 100% complete. We should note that the number of dopamine groups measured for the present Dopa-PIMA-based ligands are much higher than that for OligoPEG-Dopa ligand (~6 dopamines per chain) we reported earlier using polyacrylic acid as a precursor polymer. See reference 40. This is true even if we account for the difference in molecular weights between the two polymer precursors used (PAA has an index of polymerization of 25), which confirms the advantages offered by the new platform for the synthesis of multidentate ligands.

III. Ligand Exchange and Characterization of Aqueous Fe$_3$O$_4$ NP Dispersions In some embodiments, the invention provides a composition comprising a core nanoparticle material coated with a polymer ligand according to the present invention. A nanoparticle is generally a spherically shaped material having a diameter generally between about 1 nanometer and about 10,000 nanometers in diameter, such as between about 1 nanometer and about 2500 nanometers in diameter, or between about 1 nanometer and about 1000 nanometers in diameter, or between about 1 nanometer and about 100 nanometers in diameter. In some embodiments, the nanoparticle comprises a magnetic material. In some embodiments, the nanoparticle comprises a non-magnetic material. In some embodiments, the nanoparticle comprises a material selected from the group consisting of Fe$_3$O$_4$, Fe$_2$O$_3$, FePt, Co, Mn-doped Fe$_3$O$_4$, CdSeS/ZnS, InP/ZnS, PbS, CdTe, CoPt, FeCoPt, CoFe$_2$O$_4$, MnO, Mn$_3$O$_4$, Co$_3$O$_4$, FeO, Ni, TiO$_2$, Al$_2$O$_3$, CdSe, PbSe, ZrO$_2$, ZnO, Au, Ag, and graphene oxide.

According to the present invention, nanoparticles may be capped or enclosed in a shell structure comprising the polymer of the present invention. Capping or enclosing the nanoparticle may occur by contacting a nanoparticle with a polymer of the present invention. In some embodiments, the polymer ligand of the present invention may displace an organic molecule, such as an oleic acid, that caps or encloses the nanoparticle. The organic molecule which caps the nanoparticle is often hydrophobic, and the nanoparticle may be dispersed in a hydrophobic solvent. By carrying out a ligand exchange reaction, the polymer of the present invention may convert a hydrophobic particle into a hydrophilic particle.

Figure 2:
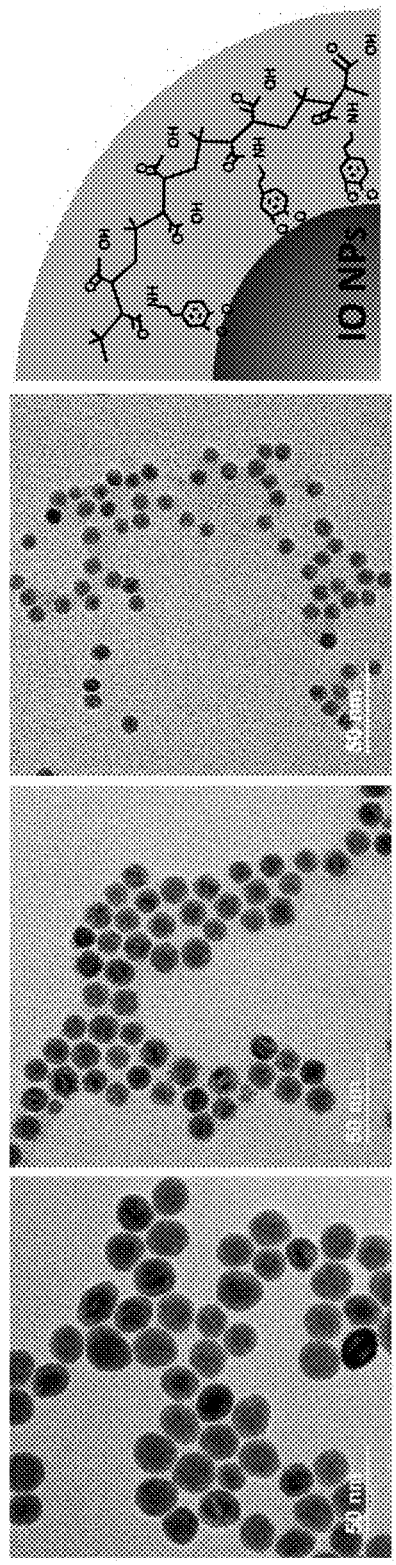
FIGS. 2A, 2B, and 2C are TEM images of iron oxide nanoparticles with 10.5 nm (FIG. 2A), 8.0 nm (FIG. 2B) and 4.6 nm (FIG. 2C) core radius after ligand exchange with Dopa-PIMA.
FIG. 2D is a depiction of the iron oxide particles comprising Dopa-PIMA capping groups.
Figure 3:
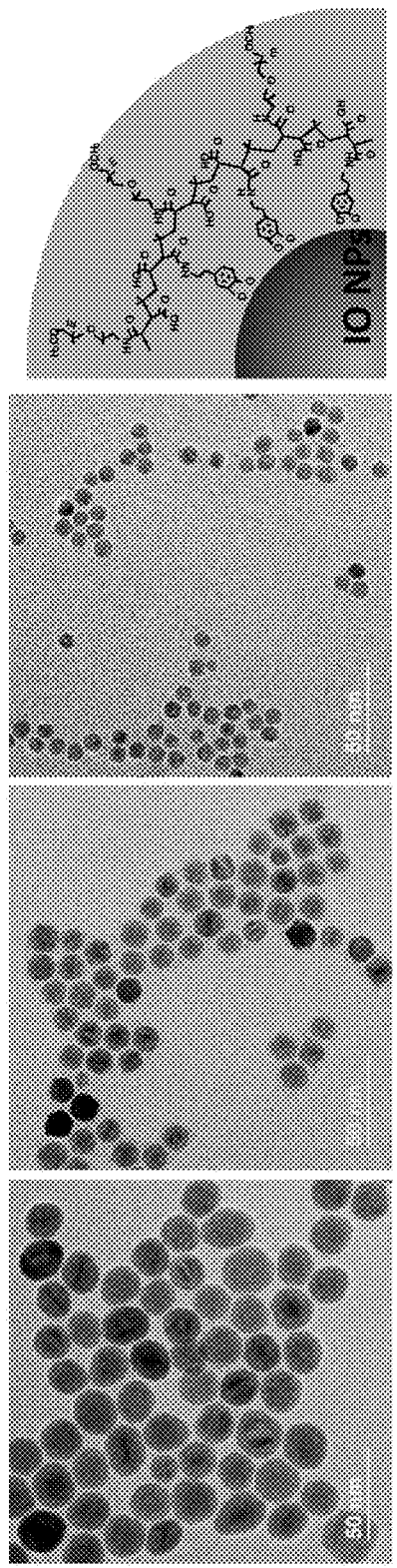
FIGS. 3A, 3B, and 3C are TEM images of iron oxide nanoparticles with 10.5 nm (FIG. 3A), 8.0 nm (FIG. 3B) and 4.6 nm (FIG. 3C) core radius after ligand exchange with Dopa-PIMA-PEG.
FIG. 3D is a depiction of the iron oxide particles comprising Dopa-PIMA-PEG capping groups.

Three different sets of Fe$_3$O$_4$ NPs capped with oleic acid, with average radius, R$_0$, of 10.5, 8.0 and 4.6 nm (extracted from transmission electron microscopy, TEM experiments), were synthesized using thermolysis of iron precursors as reported previously. See reference 15, the disclosure of which is hereby incorporated by reference as if set forth in its entirety. FIGS. 1A, 1B, and 1C are TEM images of iron oxide nanoparticles with 10.5 nm (A), 8.0 nm (B) and 4.6 nm (C) core radius before ligand exchange. FIG. 1D is a depiction of the iron oxide particles comprising the oleate capping groups. FIGS. 2A, 2B, and 2C are TEM images of iron oxide nanoparticles with 10.5 nm (A), 8.0 nm (B) and 4.6 nm (C) core radius after ligand exchange with Dopa-PIMA. FIG. 2D is a depiction of the iron oxide particles comprising Dopa-PIMA capping groups. FIGS. 3A, 3B, and 3C are TEM images of iron oxide nanoparticles with 10.5 nm (A), 8.0 nm (B) and 4.6 nm (C) core radius after ligand exchange with Dopa-PIMA-PEG. FIG. 3D is a depiction of the iron oxide particles comprising Dopa-PIMA-PEG capping groups. The TEM images shown in FIGS. 1-3 indicate that these nanoparticles are spherical with uniform cores and reduced size distribution. The nanoparticles were ligated with these polymers via mixing with the oleic acid capped-Fe$_3$O$_4$ NPs in THF overnight at 50° C., followed by purification. Room temperature can also be used but longer incubation time may be needed. The nanoparticles capped with the new ligands were readily dispersible in water. An additional purification step to remove excess free ligands and solubilized oleic acid was carried out using a membrane filtration device (see Examples). The TEM micrographs showed that nanoparticles capped with Dopa-PIMA or Dopa-PIMA-PEG maintain their overall size after surface modification with no sign of shape change or aggregation. See FIGS. 2 and 3. Ligand exchange with these amphiphilic polymers is also highly efficient and results in minimal to no loss (less than 10%) of materials after the phase transfer to water.

Dynamic light scattering (DLS) data indicate that after ligand-exchange the nanoparticles have narrow size distribution with low polydispersity index values (PDI≤0.1). See Table 1 below. The hydrodynamic radii (R$_H$) measured for the three dispersions of Fe$_3$O$_4$ NPs capped with the native oleic acid in toluene were 16.7, 13.1 and 7.9 nm, respectively. See Table 1. This indicates that the ratio of sizes extracted from DLS and TEM, R$_H$/R$_0$, is ~1.5-1.6, in agreement with what is expected for such hard spheres and consistent with data reported for other materials. See reference 43. The corresponding hydrodynamic sizes measured for NPs capped with Dopa-PIMA dispersed in water were 22.0, 19.2 and 14.4 nm, while those sizes measured for NPs capped with Dopa-PIMA-PEG were equal to 24.6, 20.6, and 15.3 nm, respectively. See Table 1. The phase transfer using these Dopa-PIMA-based ligands increases the hydrodynamic size of the IO NPs by ~6-7 nm. Effects of introducing PEG groups added ~2 nm to the measured size on average compared to Dopa-PIMA ligands. This increase is significantly smaller than those measured for IO NPs surface-functionalized with a silica shell, or an organic cap made of either dextran or polyvinylpyrrolidone (PVP). See References 6, 44, and 45. They are also smaller than those measured for NPs capped with mono-dopamine-PEG ligands having the same chain length. See reference 46. This is likely due to the presence of some small aggregates in the mono-dopamine-PEG capped NPs; these ligands cannot confer the same long-term colloidal stability to the NPs as multidentate dopamine ligands (e.g., Dopa-PIMA-PEG) are able to do.

TABLE 1

| Core Radius, $R_0$ (nm), measured by TEM | Oleic Acid-Capped | | Dopa-PIMA-capped | | Dopa-PIMA-PEG-capped | |
|---|---|---|---|---|---|---|
| | $R_H$ (nm) | PDI | $R_H$ (nm) | PDI | $R_H$ (nm) | PDI |
| 10.5 | 16.7 | 0.04 | 22.0 | 0.06 | 24.6 | 0.05 |
| 8.0 | 13.1 | 0.08 | 19.2 | 0.10 | 20.6 | 0.12 |
| 4.6 | 7.9 | 0.09 | 14.4 | 0.10 | 15.3 | 0.09 |

IV. Colloidal Stability Tests

Stability tests were performed of aqueous dispersions of Dopa-PIMA- and Dopa-PIMA-PEG-capped nanoparticles (10.5 nm in radius) in phosphate buffers at different pHs, in the presence of 1 M NaCl and when mixed with growth media. Similar results were obtained for the other sets of NPs. Dispersions of NPs capped with Dopa-PIMA-PEG are colloidally stable over the pH range from 4 to 12 and in the presence of 1 M NaCl for at least 6 months of storage. After 6 months, IO NPs at pH 4 started to exhibit aggregation, and macroscopic precipitation occurred after 1 year of storage. These dispersions stayed stable at pH 6-12 and in the presence of 1 M NaCl for at least 1 year storage. In comparison, dispersions of NPs capped with PEG-free ligand (e.g., Dopa-PIMA-NPs) progressively precipitated out of the solution at 1 M NaCl after 1 month of storage, along with partial aggregation observed after varying storage times for pH 4-pH 8. For instance, dispersions of Dopa-PIMA-NPs at pH 4 started to aggregate after 3 months, but no aggregate formation was observed until 1 year at pH 8. A dispersion of iron oxide (IO) nanoparticles (NP) capped with these two ligands stayed stable and aggregate-free for at least one month in 100% growth media (RPMI-1640).

The DLS measurements further complement the above colloidal stability data. While a fixed hydrodynamic size was measured for the Dopa-PIMA-PEG-capped NPs (Dopa-PIMA-NPs) across the full pH range and in 1 M NaCl for the three-month test period, a sizable increase in $R_H$ was measured for Dopa-PIMA-NPs in pH 4 buffer and in 1 M NaCl solution. At pH 4, the hydrodynamic size of Dopa-PIMA-NPs progressively increased from ~22 nm to ~29 nm after one month and to 39 nm after 3 months. Similarly, $R_H$ increased to about 60 nm for Dopa-PIMA-NPs dispersed in 1 M NaCl after one month of storage. The weaker stability of Dopa-Dopa-PIMA-NPs may be attributed to protonation of the carboxylic groups at lower pH, and screening of the electrostatic repulsions by counterions in the presence of 1 M NaCl. This confirms that for these PEG-free ligands, colloidal stabilization of the NPs is driven by electrostatic repulsions. However, incorporating PEG moieties into polymer ligand expands the range of colloidal stability conditions. Similar long term colloidal stability data to pH changes and in the presence of excess salt were collected for the other size nanoparticles. Iron oxide nanoparticles exchanged with mono-Dopa-PEG described in reference 40 were limited in stability. In those experiments, precipitation took place after 1 day at pH 4 and after 1 month at pH 11. NPs capped with OligoPEG-Dopa presenting ~6 dopamines per chain, were stable for one month at pH 4 and 12, and for 2 months in 1 M NaCl solution.

V. Nanoparticle Functionalization

Direct attachment of biomolecules to the NP surfaces, driven by metal-coordination, has been applied to attach peptides, proteins and DNA to Au nanoparticles and QDs. In particular, a variety of thiol-modified oligonucleotides and peptides have been immobilized on Au nanoparticles and QDs. See reference 47. Similarly, polyhistidine-tagged proteins and peptides have also been immobilized onto QD surfaces. See reference 48. However, direct use of such strategy to attach biomolecules to iron oxide NPs has been much less effective. Conjugation of biomolecules to NPs via electrostatic interactions has been reported, but this mode of coupling is sensitive to pH, soluble ions and proteins in the medium. See references 19 and 49. Covalent linking of biomolecules to functional groups on the NP surface is thus preferable, and commonly suitable groups include amines, carboxylic acids and thiols. See references 19 and 50. They can be used for implementing coupling strategies such as carboxyl-to-amine or thiol-to-amine (via a maleimide linker).

With the robustness and compactness of Dopa-PIMA-PEG capped NPs established, we turned our attention to the goal of incorporating chemical functionalities in the ligand. This can be achieved in the present design by simply replacing a fraction of the methoxy terminated amino-PEG ($H_2N$-PEG-OMe) with terminally reactive moieties ($H_2N$-PEG-R with R=azide, amine or lipoic acid). For example, using a mixture of 15:35 $H_2N$-PEG-$N_3$:$H_2N$-PEG-OMe (as a percentage) during the addition reaction we prepared azide-modified ligand with ~6 azide groups per chain. This can provide NPs that are compatible with azide-alkyne cycloaddition (CLICK) coupling to target biomolecules, including DNA, peptides and proteins. See reference 50. We have also prepared thiol-modified Dopa-PIMA-PEG ligands by substituting a fraction of $H_2N$-PEG-OMe with $H_2N$-PEG-LA during the addition reaction. Reduction of the LA groups (e.g., chemically) would provide thiol-presenting polymer ligands. Insertion of azide and lipoic acid were verified using FT-IR and $^1H$ NMR spectroscopy, respectively. For instance, the FTIR spectrum of Dopa-PIMA-PEG-azide showed a clearly defined vibration band at 2108 $cm^{-1}$ (ascribed to azide), while the multiple peaks at 1.3-2.4 ppm and 3.1-3.2 ppm measured in the $^1H$-NMR spectrum of Dopa-PIMA-PEG-LA ligand are ascribed to the lipoic acid protons.

Figure 4:
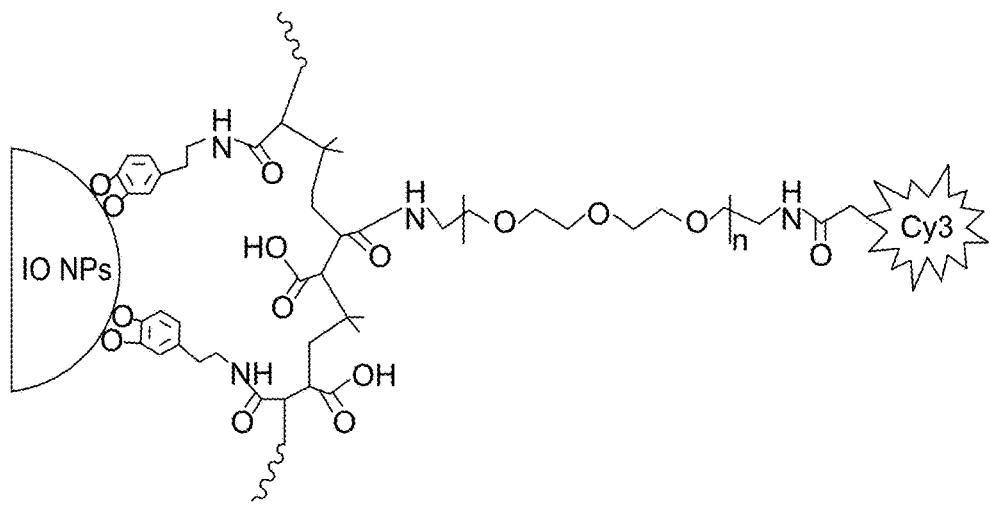
FIG. 4 is a depiction of iron oxide nanoparticle ligand exchanged with NHS-ester modified sulfo-Cy3 Dopa-PIMA-PEG-amine.
Figure 5:
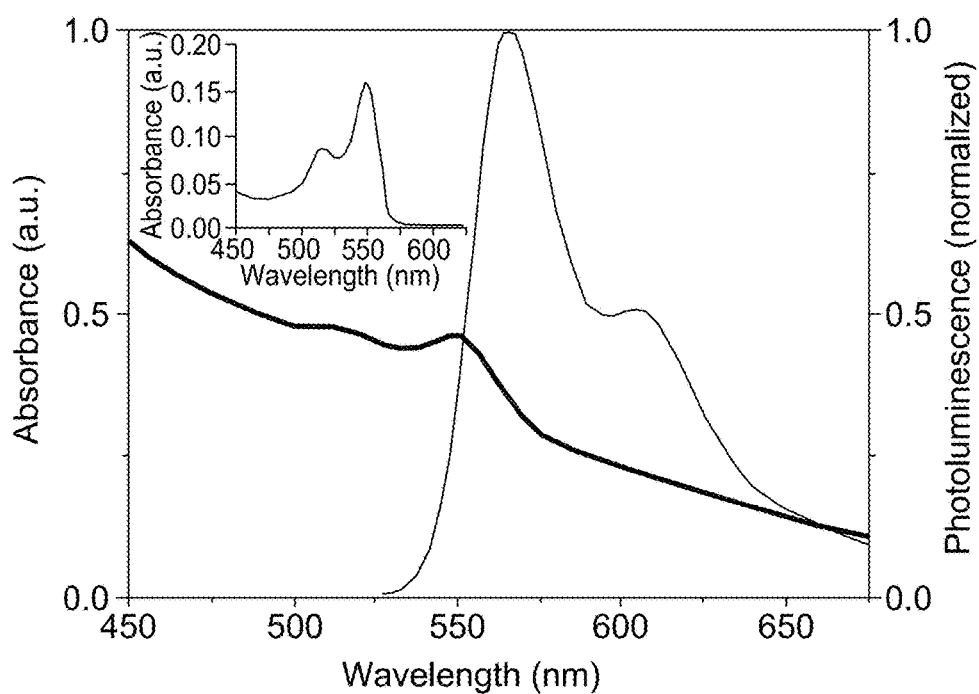
FIG. 5 is a graph showing the absorption and emission spectra collected from the $Fe_3O_4$-Cy3 conjugates after purification.

The synthesis of the Dopa-PIMA-PEG-amine ligand was carried out using a small modification to minimize potential problems associated with cross-linking that may be caused by reaction of the two amine groups in a $H_2N$-PEG-$NH_2$ chain with anhydride rings on separate polymer backbones. The nucleophilic addition reaction was carried out in two steps: the mixture of dopamine and $H_2N$-PEG-OMe was first added to PIMA solution, and then after three hours, the desired amount $H_2N$-PEG-$NH_2$ (e.g., 15%) was added. To prove that this route provides amine-reactive $Fe_3O_4$ NPs, we conjugated NHS-ester modified sulfo-Cy3 to NPs ligand-exchanged with Dopa-PIMA-PEG-amine (15% amine) See FIG. 4, which is a depiction of iron oxide nanoparticle ligand exchanged with NHS-ester modified sulfo-Cy3 Dopa-PIMA-PEG-amine FIG. 5 is a graph showing the absorption and emission spectra collected from the $Fe_3O_4$-Cy3 conjugates after purification. There is a clear contribution from the dye to the measured absorption spectrum at 549 nm and a well-defined fluorescence signature with a maximum at 566 nm, both are characteristic of the Cy3 dye (see insert in FIG. 5).

VI. Cell Imaging

FIGS. 6A through 6G are images of a representative set of fluorescence images collected from HeLa cells incubated with the $Fe_3O_4$-Cy3 conjugates. FIGS. 6A through 6C are confocal laser scanning microscopy images of HeLa cells incubated with 4'-6-diamidino-2-phenylindole (DAPI) and $Fe_3O_4$-Cy3 for 1 hour. FIG. 6A is an image of nuclei stained with blue 4'-6-diamidino-2-phenylindole (DAPI). FIG. 6B is an image of spot-like yellow fluorescence showing internalized $Fe_3O_4$-Cy3. FIG. 6C is a merged image of blue (DAPI) and yellow ($Fe_3O_4$-Cy3) signals. Scale bar=20 μm. FIGS. 6D through 6G are confocal laser scanning microscopy images of HeLa cells incubated with 4'-6-diamidino-2-phenylindole (DAPI), $Fe_3O_4$-Cy3 conjugates, and transferrin-Cy5 (as endosome-specific marker) for 1 h. FIG. 6D is an image of nuclei stained with blue 4'-6-diamidino-2-phenylindole (DAPI). The distribution of patterns containing $Fe_3O_4$-Cy3 (FIG. 6E, yellow) was co-localized with those of the Cy5-transferrin (FIG. 6F, red). Scale bar=20 μm. FIG. 6G is a merged image of blue (DAPI), yellow ($Fe_3O_4$-Cy3), and red Cy5-transferrin signals.

The images show the distribution of cell nuclei, stained with DAPI (FIG. 6A, 6D), the yellow signal associated with the distribution of $Fe_3O_4$-Cy3 (FIG. 6B, 6E), together with the Cy5-transferrin (FIG. 6F, red) as late endo-lysosomal marker. These images show that the yellow fluorescence from the $Fe_3O_4$-Cy3 conjugates is dispersed throughput the cell cytoplasm and none is found in the nucleus. They also show that the yellow conjugates mostly are co-localized with the distribution of endo/lysosomal compartments (see yellow and red superposed images shown in FIG. 6G), indicating that the $Fe_3O_4$-Cy3 have been primarily internalized via endocytosis. This type of non-receptor-mediated endocytosis is observed frequently in HeLa cells and seems to be a general process occurring in various cells upon ingestion of nanoparticles without having surface-grafted agonists; longer incubation times and rather high concentrations of reagents (e.g., μM for QDs) are needed, nonetheless. See References 45, 51, and 52.

VII. In Vitro Cytotoxicity Evaluation

Figure 7:
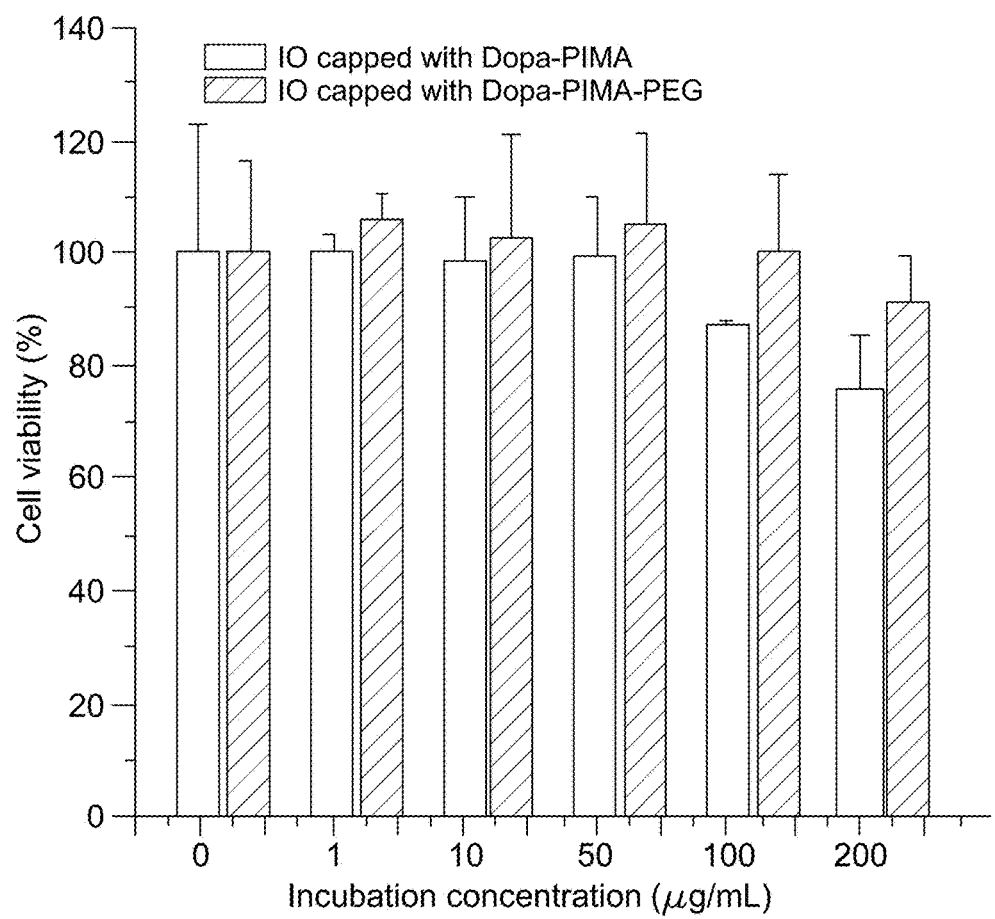
FIG. 7 is a graph showing MTT viability test of HeLa cells incubated with varying concentrations of $Fe_3O_4$ NP-capped with the various PIMA-based ligands. NPs with 10.5 nm in radius have been used.

We assessed the cytotoxicity of the Dopa-PIMA and Dopa-PIMA-PEG stabilized $Fe_3O_4$ nanoparticles (10.5 nm size in radius) using MTT (3-(4,5-dimethylthiazol-2-yl)-2,5-diphenyltetrazolium bromide) assay on human cervix carcinoma cell line (HeLa cell). FIG. 7 shows that the viability of cells incubated with Dopa-PIMA-PEG-$Fe_3O_4$ NPs essentially remained at 100% throughout the range of concentrations used. In comparison, the viability of cells incubated with Dopa-PIMA-capped $Fe_3O_4$ NPs slightly decreased to 70-80% at reagents concentrations exceeding 100-200 μg/mL. These results indicate that overall NPs capped with the polymer ligand containing PEG moieties induces minimal to no toxicity to cell cultures. This result is consistent with other measurements showing marginal toxicity of iron oxide NPs to various cells.

VIII. Relaxivity Measurements

The accumulation of IO NPs within tissues results in strong contrast effects in MRI scans. When dispersed in aqueous solutions or in a biological tissue and in the presence of an external magnetic field, the superparamagnetic NPs create microscopic field inhomogeneities that affect the spins of neighboring water molecules. See references 5 and 53. The diffusion of water molecules into these zones of magnetic inhomogeneities affects a large number of water molecules, inducing the activation of spin dephasing (contrast effect) which is primarily measured as a shortening of the spin-spin relaxation times ($T_2$) or an increased in the spin-spin relaxation rates ($r_2$). The size of the IO NP plays a key role in the effective contrast values. At the nanoscale, single magnetic domains are developed, and each with a corresponding magnetic moment that is aligned in a particular direction defined by the magnetic anisotropy values of the NP. Within the range (1-20 nm), surface spins tend to be slightly tilted, forming a magnetically disordered spin-glass-like "surface layer". See reference 53. This surface effect significantly influences the magnetic moments and in turn alters the $T_2$ relaxation of neighboring water molecules. Moreover, this effect is strongly dependent on NP size. See references 18 and 53. As the size decreases, the surface effect becomes more pronounced, resulting in the reduced net magnetic moment and therefore influencing the spin-spin relaxation ($r_2$) of the water protons. The general trend is that as the size of the IO NP increases, the $T_2$ relaxation time in same concentration decreases and $r_2$, defined as the slope of $1/T_2$ against Fe concentration, increases. See reference 18. IO NPs with higher $r_2$ values exhibit detectable $T_2$ changes and contrast effect with fewer nanoparticles as opposed to IO NPs with lower $r_2$ values. Thus, we reasoned that the $r_2$ values of the IO NPs with radius of 10.5 nm, should be larger than that of those IO NPs with lower radius. Plots of the relaxation rates ($1/T_2$) for the corresponding $Fe_3O_4$ NPs capped with the various Dopa-PIMA-modified ligands as a function of Fe concentration show a linear behavior for all the samples tested. Furthermore, the $r_2$ value for the Dopa-PIMA-PEG capped IO NPs increased from 68.6 to 109.1 and 172.0 $mM^{-1}s^{-1}$, as the size changed from 4.6 nm to 8.0 and then 10.5 nm. See Table 12. Similarly, the $r_2$ values rose from 40.1 to 118.2 and 193.7 $mM^{-1}s^{-1}$ for Dopa-PIMA capped IO NPs as the nanoparticle size increased. These IO NP core size dependent $r_2$ values are comparable to or even higher than those reported for other $Fe_3O_4$-type magnetic nanoparticles in the literature. See references 6, 44, and 54.

TABLE 2

Relaxivity values extracted from plots of the $T_2$ relaxation time vs NP concentration of Dopa-PIMA- and Dopa-PIMA-PEG-stabilized $Fe_3O_4$ nanoparticles with the three different sizes: 4.6, 8.0 and 10.5 nm.

| Core Radius, $R_o$ (nm), from TEM | $r_2$ ($mM^{-1}s^{-1}$) Dopa-PIMA-capped | $r_2$ ($mM^{-1}s^{-1}$) Dopa-PIMA-PEG-capped |
|---|---|---|
| 4.6 | 40.1 | 68.6 |
| 8.0 | 118.2 | 109.1 |
| 10.5 | 193.7 | 172.0 |

IX. Conclusion

In some embodiments, the present invention is directed to new class of multi-coordinating amphiphilic polymers ideally adapted for surface-functionalizing iron oxide nanoparticles. The ligand design relies on the specific and highly efficient nucleophilic addition between amine and maleic anhydride. Using this scheme we were able to insert controllable numbers of amine-presenting anchoring hydrophilic and reactive groups onto a poly(isobutylene-alt-maleic anhydride) chain using one step reaction and without the need for additional coupling reagents or excess amine-presenting precursors. This provided a set of polymer ligands that present multiple dopamine anchors along with several hydrophilic and reactive PEG moieties. Ligand exchange of hydrophobic iron oxide nanoparticles with these ligands is rapid and provides aggregate-free hydrophilic dispersions of NPs with great long-term colloidal stability over a broad range of pH values (pH 4-12) and in the presence of large excess of electrolytes, as verified by light scattering measurements and stability in growth media. The hydrophilic nanoparticles are compact in size and reactive with target molecules. We have also assembled an MRI-optical dual-mode probe via covalent conjugation of amine-functionalized $Fe_3O_4$ NPs with sulfo-Cy3 NHS ester dye, and utilized them in the fluorescence imaging of live cells with good bio-distribution. Furthermore, $T_2$ relaxation measurements of these dispersions showed that the relaxivity coefficient, $r_2$, for these materials exhibit a consistent magnetic resonance enhancement with nanocrystal size. This opens up the possibility for using these magnetic platforms for use as MRI contrast agents to image cells and tissues and for designing specific biosensors. These materials can be easily integrated into the design of additional multimodal platforms. Finally, we would like to stress the present ligand design can be easily adapted to a variety of other inorganic nanocrystals, such as quantum dots and metal nanoparticles. Some of those approaches are being explored in our laboratory and will be discussed in future work(s).

X. Examples

The following non-limiting examples are provided to further illustrate the present invention.

Example 1

Materials

Poly(isobutylene-alt-maleic anhydride) (PIMA) (average Mw: 6000 Da), Poly(ethylene glycol) (PEG) (average Mw: 600 Da), poly(ethylene glycol) methyl ether (average Mw: 750 Da), dopamine hydrochloride, dimethylformamide (DMF), triethylamine, lipoic acid, sodium azide, RPMI-1640 growth media, along with most of the chemicals used were purchased from Sigma Aldrich (St Louis, Mo.). Sulfo-Cy3 NHS ester and PD10 columns were purchased from Lumiprobe (Hallandale Beach, Fla.). Solvents were purchased from Sigma Aldrich (St Louis, Mo.). Column purification chromatography was performed using silica gel (60 Å, 230-400 mesh) acquired from Bodman Industries (Aston, Pa.). Deuterated solvents used for NMR experiments were purchased from Cambridge Isotope Laboratories (Andover, Mass.). The chemicals and solvents were used as received unless otherwise specified. All syntheses were carried out under N2 passed through an O2 scrubbing tower unless otherwise stated. Air sensitive materials were handled in an MBraun Labmaster glovebox, and standard Schlenk techniques were used in manipulation of air-sensitive solutions.

Example 2

Characterization $^1$H NMR spectra of the ligands were recorded using a 600 MHz spectrometer (Bruker SpectroSpin, Billerica, Mass.). Transmission electron microscopy (TEM) images were taken using a 200 kV JEOL-2010 instrument or a Philips FEI CM-120 operating at an acceleration voltage of 120 kV. Samples for TEM were prepared by drop casting the NP dispersion onto the holey carbon film on a fine mesh Cu grid (400 mesh). Dynamic light scattering measurements were carried out using ALV/CGS-3 Compact Goniometer System (ALV-GmbH, Langen, Germany). This system is equipped with a HeNe laser (illuminated at 632.8 nm), ALV photon correlator and an avalanche photodiode for signal detection. The scattered signal can be detected at angles ranging from 15 to 150 degrees. Each scattered pattern used for analysis was the average result of 3 acquisition periods of 10 seconds each. FT-IR spectra of the purified compounds were collected using a Spectrum 100 FTIR Spectrometer (PerkinElmer, Waltham, Mass.). Optical absorption data of dye-conjugated NPs was collected using an UV-Vis absorption spectrophotometer (UV 2450 model, Shimadzu, Columbia, Md.). The fluorescence spectra were collected using a Fluorolog-3 spectrofluorometer (HORIBA Jobin Yvon, Edison, N.J.) equipped with PMT and CCD detectors. Solvent evaporation was carried using a rotary evaporator R-215 (Buchi, New Castle, Del.). The absorption data for the MTT assay were collected using a microplate reader (Infinite M1000 from Tecan, Durham, N.C.).

Example 3

Synthesis of Amine-Terminated Inert and Reactive Poly(Ethylene Glycol) Precursors The precursors $H_2N$-PEG750-OCH$_3$, $H_2N$-PEG600-N$_3$, $H_2N$-PEG600-NH$_2$, $H_2N$-PEG600-LA were synthesized in our laboratory starting from poly(ethylene glycol) methyl ether (average Mw~750 Da), and poly(ethylene glycol) (average Mw~600 Da), following the procedures detailed in previous publications. See References 56-59.

Example 4

Synthesis of Dopamine-Modified PIMA (Dopa-PIMA)

In a 50 mL three-neck round-bottom flask equipped with an addition funnel and a magnetic stirring bar, 0.385 g of poly(isobutylene-alt-maleic anhydride) (PIMA, Mw~6000 g/mol, 2.5 mmol monomer units) was dissolved in 10 mL DMF. The flask was purged with nitrogen for 10-15 minutes and the solution was heated up to 70° C. In a separate vial, 0.237 g of dopamine hydrochloride (1.25 mmol) was dissolved in 2 mL DMF, to which an equivalent molar amount of triethylamine was added. The solution became turbid, and was stirred for two hours at room temperature and under nitrogen atmosphere to allow for dopamine activation, followed by centrifugation to remove the formed salts (e.g., triethylamine hydrochloride). The supernatant was loaded into the additional funnel, and added dropwise to the flask containing the PIMA solution. Once the addition was complete, the reaction mixture was further stirred for overnight at 70° C. After removing the DMF under vacuum, DI water was added to precipitate the product, which was washed with 1 M HCl solution (3-4 times), followed by a final rinse with DI water. Lyophilization of the solution yielded the product as a white powder.

Example 5

Synthesis of Dopamine- and PEG-Modified PIMA (Dopa-PIMA-PEG)

0.385 g of PIMA (2.5 mmol monomer units) was dissolved in 10 mL of DMF in a 50 mL three-necked round-bottomed flask equipped with an additional funnel and a magnetic stirring bar. The solution mixture was purged with nitrogen and then heated to 70° C. Separately, a mixture of amino-PEG (H$_2$N-PEG-OMe, 0.995 g, 1.25 mmol) and dopamine (0.237 g, 1.25 mmol) activated using triethylamine (as described above) was prepared in 4 mL DMF. This content was loaded into the addition funnel, and then added dropwise to the PIMA solution. When the addition was complete, the reaction mixture was further stirred at 70° C. overnight. The DMF was removed under vacuum, and then 3 mL of chloroform was added. The solution was purified by silica column chromatography using chloroform as the eluent. Following solvent evaporation, gel-like yellow oil was collected as the final product.

Example 6

Synthesis of Reactive Dopa-PIMA-PEG (Dopa-PIMA-PEG-R)

Here we follow the same synthetic steps used for preparing Dopa-PIMA-PEG above, but substitute a fraction of H$_2$N-PEG-OMe with H$_2$N-PEG-R (R is an azide or a disulfide). We briefly describe the synthesis of azide-functionalized Dopa-PIMA-PEG. 0.385 g of Poly(isobutylene-alt-maleic anhydride) (2.5 mmol monomer units) was dissolved in 10 mL DMF and loaded into a 50 mL three-necked round-bottomed flask equipped with an addition funnel. The flask was purged with nitrogen and the solution heated up to 70° C. A separately prepared mixture of dopamine (0.375 g, 1.25 mmol) activated with triethylamine, H$_2$N-PEG-OMe (0.70 g, 0.875 mmol) and H$_2$N-PEG-N$_3$ (0.247 g, 0.375 mmol) dissolved in 4 mL DMF was loaded onto the addition funnel then added dropwise to the polymer solution. The reaction mixture was stirred overnight at 70° C. under nitrogen. After removing the DMF under vacuum, 3 mL of chloroform was added, and the product was purified by silica column chromatography using chloroform as the eluent. The product as a yellow viscous liquid was obtained following solvent evaporation. Additional details on ligands with other functional groups are provided in the Supporting Information.

Example 7

Synthesis of Dopa-PIMA-PEG-LA

To synthesize lipoic acid functionalized polymer ligand, we used the same synthetic steps as we prepared azide-functionalized Dopa-PIMA-PEG. 0.385 g of Poly(isobutylene-alt-maleic anhydride) (2.5 mmol monomer units) was dissolved in 10 mL DMF and loaded into a 50 mL three-necked round-bottomed flask equipped with an addition funnel and a magnetic stirring bar. The flask was purged with nitrogen and the solution heated up to 70° C. A separately prepared mixture of dopamine (0.375 g, 1.25 mmol) activated with triethylamine, H$_2$N-PEG-OMe (0.4 g, 0.5 mmol) and H2N-PEG-LA (0.59 g, 0.75 mmol) dissolved in 4 mL DMF was loaded into the addition funnel then added dropwise to the polymer solution. The reaction mixture was stirred overnight at 70° C. under nitrogen. After removing the DMF under vacuum, 3 mL of chloroform was added, and the product was purified by silica column chromatography using chloroform as the eluent.

Example 8

Synthesis of Dopa-PIMA-PEG-Amine

A modified synthetic route was used for preparing amine-functionalized Dopa-PIMA-PEG. 0.385 g of Poly(isobutylene-alt-maleic anhydride) (2.5 mmol monomer units) was dissolved in 10 mL DMF and loaded into a 50 mL three-necked round-bottomed flask equipped with an addition funnel and a magnetic stirring bar. The flask was purged with nitrogen and the solution heated up to 70° C. A separately prepared mixture of dopamine (0.375 g, 1.25 mmol) activated with triethylamine, and H$_2$N-PEG-OMe (0.7 g, 0.875 mmol) dissolved in 2 mL DMF was loaded into the addition funnel then added dropwise to the polymer solution. After the addition was complete and the mixture was reacted for 3 hours, H$_2$N-PEG-NH$_2$ (0.22 g, 0.375 mmol) dissolved in 2 mL DMF was loaded into the additional funnel and added dropwise to the mixture. The reaction mixture was stirred overnight at 70° C. under nitrogen. After removing the DMF under vacuum, 3 mL of chloroform was added, and the product was purified by silica column chromatography using chloroform as the eluent.

Example 9

Synthesis of Iron Oxide Nanoparticles

We followed the synthetic scheme described in reference 15, the disclosure of which is hereby incorporated by reference as is set forth in its entirety. Briefly, to synthesize the iron-oleate complex (i.e., precursor), 3.6 g of FeCl$_3$.6H$_2$O and 12.2 g of sodium oleate were dissolved in a solvent mixture made of 26 mL ethanol, 20 mL DI water and 46 mL hexane. The mixture was heated to 70° C. for four hours. Then the upper layer containing the iron-oleate complex in hexane was washed with distilled water three times, and the hexane was evaporated, yielding the iron-oleate complex as brown oil.

Growth of the iron oxide nanoparticles relied on the reduction of iron-oleate at high temperature. Briefly, 3.6 g Fe-oleate complex and 0.57 g of oleic acid were dissolved in 20 g of 1-octadecene. The mixture was heated (at a constant heating rate of 3.3° C./min) to 320° C., then the solution was maintained at that temperature for 30 min; these conditions provided a dispersion of 8.0 nm (radius) iron oxide nanoparticles. Nanoparticles with additional sizes are grown by changing the annealing temperature, as previously described in Reference 15.

Example 10

Ligand Exchange of Fe$_3$O$_4$ Nanoparticles

A typical ligand exchange and phase transfer is carried out as follows. 1 mL of growth dispersion in hexane was precipitated using ethanol. The turbid solution was centrifuged and the supernatant discarded, providing ~5 mg of nanoparticles as a wet pellet. The precipitate containing the nanoparticles was dispersed in 0.5 mL THF, and then further mixed with 1 mL THF containing 25 mg of solubilized Dopa-PIMA-PEG. The vial was sealed, the atmosphere switched to nitrogen and stirred for overnight at 50° C. using an oil bath. The sample was precipitated using excess hexane and centrifuged at 3900 RPM for 4 min to provide a dark pellet. The clear supernatant was discarded, and the pellet re-dissolved in a mixture of 0.5 mL THF and 0.3 mL ethanol, followed by precipitation by adding excess hexane. The turbid dispersion was centrifuged, the supernatant was discarded and the residual precipitate was dried under vacuum to yield a dark pellet, which was easily dispersed by adding 1-2 mL of DI water. After sonication, the aqueous dispersion was filtered with a 0.45 μm disposable syringe filter, then excess free ligands were removed by applying 3-4 rounds of concentration/dilution (DI water) using a centrifugal filtration device (Millipore, Mw cutoff=100 kDa). A similar protocol was applied to ligand exchange with Dopa-PIMA-PEG-R. Ligand exchange with Dopa-PIMA followed the same steps described for Dopa-PIMA-PEG, but the ligand was dissolved in THF mixed with a few drops of ethanol, and the dry pellet after ligand exchange was first dissolved in buffer (pH 8) with sonication.

Example 11

Dynamic Light Scattering (DLS) Measurements

The hydrodynamic size of the iron oxide nanoparticles, either capped with their native ligands dispersed in toluene, or cap-exchanged with Dopa-PIMA or Dopa-PIMA-PEG ligands (dispersed in buffer media, pH=7.5) were measured using an ALV/CGS-3 Compact Goniometer System. All the dispersions were filtered through a 0.22 μm disposable filter (Millipore) before collecting the scattered signal. The signal was collected at angles varying between 60 and 120 degrees. Each scattered pattern was the average result of 3 acquisition periods of 10 seconds each. The intensity count rates were maintained at ~150-300 Hz, achieved through appropriate control over the NP concentrations for the various nanoparticle sizes used. The resulting auto-correlation function was fitted to a cumulant series using ALV-7004 correlator software. For every sample we verified that the measured hydrodynamic size (extracted from the Laplace transform of the auto-correlation function) is independent of the scattering angle, as anticipated. See references 43 and 55. The data on the hydrodynamic size reported here were collected at 90 degree scattering angle. To track possible changes in the NP size for a particular dispersion with time, the signal was collected and analyzed at different time intervals.

Example 12

Covalent Conjugation of Sulfo-Cy3 NHS Ester to Polymer-Ligated $Fe_3O_4$ NPs

We detail the procedure for conjugating iron oxide nanoparticles (10.5 nm in radius) capped with amine-modified Dopa-PIMA-PEG (i.e., 15% of the PEG moieties had terminal amines) with sulfo-Cy3 NHS ester. Briefly, 200 μL of amine-functionalized NPs (amine-$Fe_3O_4$ NPs, concentration ~2 mg/mL) were first dispersed in 300 μL phosphate buffer (pH=7.5) and stirred for 1 h. Then 5-8 times excess sulfo-Cy3 NHS ester initially dissolved in 50 μL DMSO was added and the mixture was left to react at room temperature for 2 hours, then overnight at 4° C. Excess unreacted dye was removed by size exclusion using a PD 10 column (GE Healthcare). The conjugate was characterized using absorption and fluorescence spectroscopy.

Example 13

Fluorescence Imaging of Live Cells

HeLa cell cultures (human cervix carcinoma cell line, provided by the FSU cell culture facility) were grown at 37° C. in a humidified 5% $CO_2$ atmosphere at 37° C., as a monolayer in a complete growth medium (Dulbecco's Modified Eagle's Medium, DMEM, Cellgro); the medium was supplemented with 10% (v/v) fetal bovine serum (Gibco), 4.5 g/L glucose, L-glutamine, sodium pyruvate, 1% (v/v) antibiotic-antimycotic 100× (Gibco), and 1% (v/v) non-essential amino-acid solution 100× (Sigma). $8 \times 10^4$ of the above cells were first seeded onto 18 mm circle microcover glasses (VWR) of 24-well microplates (CellStar, VWR), and the plates were placed in an incubator overnight to allow for cell attachment. After 24 hours, the cells were then mixed with Cy3-labeled $Fe_3O_4$ NPs at a concentration of 150 μg/mL of NP-Cy3 conjugates and left to incubate for 1 hour, before rinsing. After incubation the cells were washed with PBS buffer two times, fixed with 3.7% paraformaldehyde and stained with 4,6-diamino-2-phenylindole (Prolong Antifade mounting media with DAPI nuclear staining, from Invitrogen). When Cy5-transferrin as a specific endosome/lysosome marker was also used, cells were first incubated with Cy3-labeled $Fe_3O_4$ NPs at a concentration of 150 μg/mL for 1 hour. Then, after rinsing and washing with PBS buffer to remove excess Cy3-$Fe_3O_4$ conjugate, Cy5-transferrin (at 40 μg/mL) was added to the culture and incubated for 1 hour. The cells were then washed with PBS buffer two times, fixed with 3.7% paraformaldehyde and stained with 4,6-diamino-2-phenylindole. Fluorescence images were acquired from the above cultures using a confocal laser scanning microscope Leica SP2SE, DM600 equipped with acousto-optic tunable filters (AOTF) for detection. The DAPI, $Fe_3O_4$-Cy3 and Cy5-transferrin were imaged using a laser excitation at 405, 546 and 633 nm, respectively. The emission signals of DAPI, $Fe_3O_4$-Cy3 and Cy5-transferrin were collected at the optical range of 436-477 nm, 560-590 nm and 663-705 nm, respectively.

Example 14

Viability Assays

The viability of HeLa cells incubated with the NPs capped with either Dopa-PIMA or Dopa-PIMA-PEG at concentrations of 0, 1, 10, 50, 100 and 200 μg/mL, were tested using MTT assay. The MTT assay is a colorimetric test based on the cellular reduction of 3-(4,5-dimethylthiazol-2-yl)-2,5-diphenyl tetrazolium bromide (MTT, Sigma Aldrich Chemical) by the mitochondrial dehydrogenase of viable cells, forming a blue formazan product which can be measured spectrophotometrically. MTT solution was prepared at 5 mg/mL in PBS 1× and then diluted 1:5 in medium without serum or Phenol Red. Cells were first seeded into 96-well microplates ($2 \times 10^4$ cells/200 μL/well), and the plates were placed in an incubator overnight to allow adherence. After 24 hours, the nanoparticles were applied directly to the wells using a multichannel pipette (in triplicate), and the cultures were incubated for 24 h at 37° C. After incubation, the media was removed, the cells washed twice with PBS 1×, and then 200 μL of the MTT solution (0.2 mg/mL) was added to each well. After 4 h incubation at 37° C., the MTT solution was removed, and 100 μL of DMSO was added to each well to solubilize the MTT-formazan product. The absorbance at 560 nm was measured using the Infinite M1000 PRO plate reader (TECAN). The cell viability obtained from the absorbance measurements was expressed as a fraction of viable cells and normalized to that of cells that were not exposed to reagents.

Example 15

MRI Relaxometry Measurements

The $T_2$ relaxation times of the corresponding iron oxide nanoparticles suspensions were measured with a 0.47T mq20 NMR analyzer (Minispec, Bruker, Billerica, Mass.) using a CPMG pulse-echo train with a 1.5 ms interpulse spacing. For the determination of $r_2$ values, various dilutions of the corresponding iron oxide nanoparticles were prepared and their $T_2$ relaxation times measured. Then a plot of the relaxation rates ($1/T_2$) vs. the corresponding iron concentration was created. The slope for each of the plots corresponding to different iron oxide nanoparticles preparations was the value for $r_2$. Iron concentrations for each of the iron oxide nanoparticles were determined spectrophotometrically after acid digestion of the nanoparticles' suspension as previously described. See references 1 and 13.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A composition comprising a polymer comprising a repeat unit (A) and a repeat unit (G), wherein the repeat unit (A) and the repeat unit (G) have the following structures:

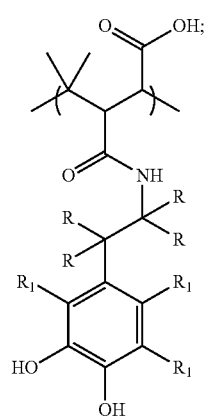

(A)

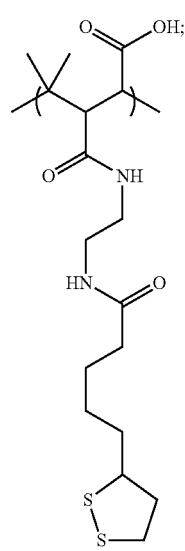

(G)

wherein each R is independently —H or —COOH, and each $R_1$ is independently —H, —NO$_2$, or —OH.

2. The composition of claim 1 wherein no more than one R is —COOH and each $R_1$ is —H.

3. The composition of claim 1 wherein the polymer comprises a repeat unit (B) having the following structure:

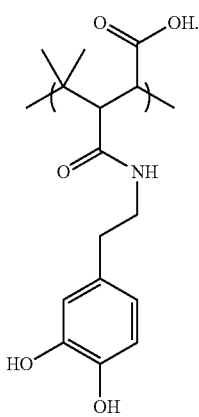

(B)

4. The composition of claim 1 wherein the polymer further comprises a repeat unit (C) having the following structure:

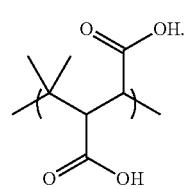

(C)

5. The composition of claim 1 wherein the polymer comprises a repeat unit (B) and a repeat unit (C) having the following structures:

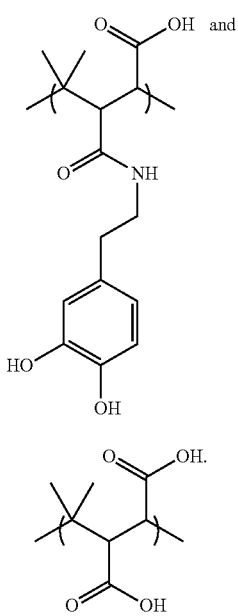

6. The composition of claim 1 wherein the polymer comprises a repeat unit (B) and further comprises a repeat unit (D) having the following structures:

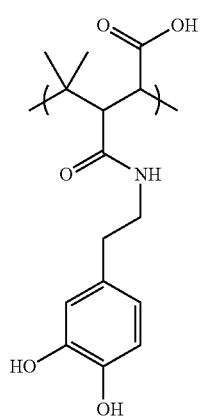

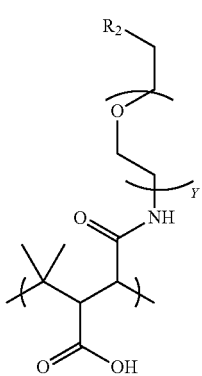

wherein Y has a value between one and about 100 and each $R_2$ is independently selected from the group consisting of hydroxy (—OH), methoxy (—OCH$_3$), amino (—NH$_2$), azido (—N$_3$), thiol (—SH), ethynyl (—C≡CH), carboxyl (—COOH), and aldehyde (—C(O)H).

7. The composition of claim 1 wherein the polymer comprises a repeat unit (B) and further comprises a repeat unit (E) having the following structures:

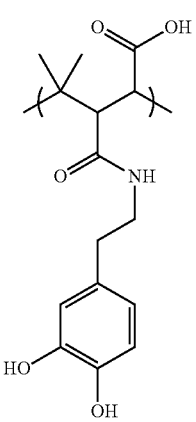

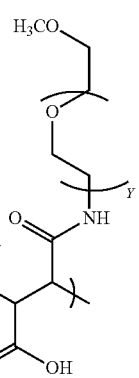

wherein Y has a value between one and about 100.

8. The composition of claim 1 wherein the polymer comprises a repeat unit (B) and further comprises a repeat unit (F) having the following structures:

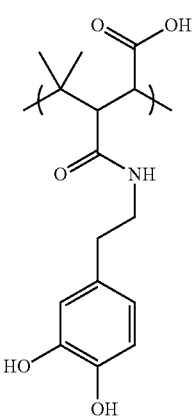

-continued

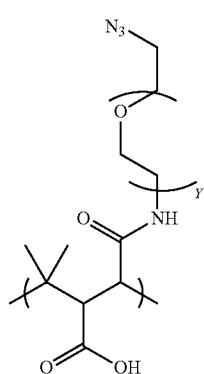
(F)

wherein Y has a value between one and about 100.

9. The composition of claim 1 wherein the polymer comprises a repeat unit (B) and further comprises a repeat unit (C) and a repeat unit (D), each having the following structures:

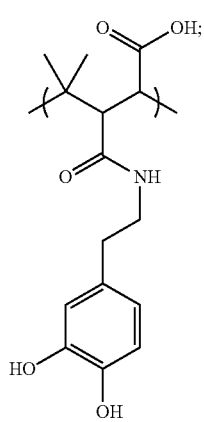
(B)

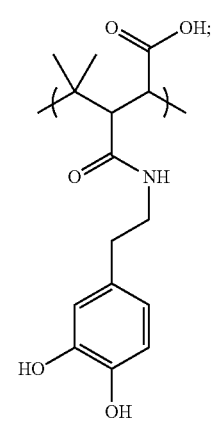
(C)

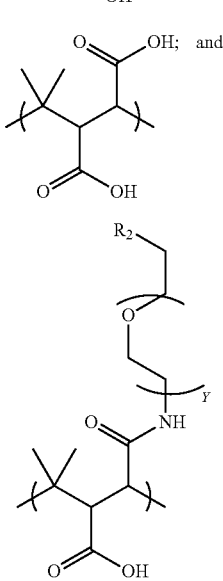
(D)

wherein Y has a value between one and about 100 and each $R_2$ is independently selected from the group consisting of hydroxy (—OH), methoxy (—OCH$_3$), amino (—NH$_2$), azido (—N$_3$), thiol (—SH), ethynyl (—C≡CH), carboxyl (—COOH), and aldehyde (—C(O)H).

10. The composition of claim 1 wherein the polymer comprises a repeat unit (B) and further comprises a repeat unit (C), a repeat unit (E), and a repeat unit (F), each having the following structures:

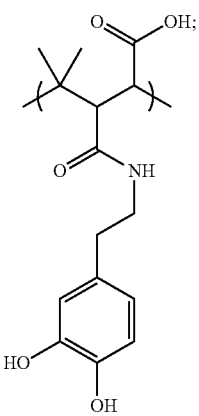
(B)

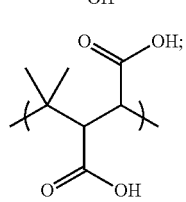
(C)

(E)

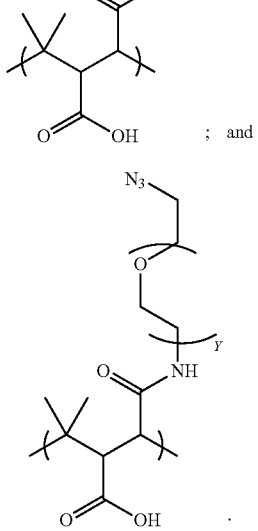
(F)

11. The composition of claim 1 wherein the polymer comprises a coating over a nanoparticle.

12. The composition of claim 11 wherein the nanoparticle comprises a magnetic material.

13. The composition of claim 11 wherein the nanoparticle comprises a material selected from the group consisting of $Fe_3O_4$, $Fe_2O_3$, FePt, Co, Mn-doped $Fe_3O_4$, CdSeS/ZnS, InP/ZnS, PbS, CdTe, CoPt, FeCoPt, $CoFe_2O_4$, MnO, $Mn_3O_4$, $Co_3O_4$, FeO, Ni, $TiO_2$, $Al_2O_3$, CdSe, PbSe, $ZrO_2$, ZnO, Au, Ag, and graphene oxide.

14. The composition of claim 11 wherein the nanoparticle comprises a material selected from the group consisting of FePt, Co, Mn-doped $Fe_3O_4$, CdSeS/ZnS, InP/ZnS, PbS, CdTe, CoPt, FeCoPt, $CoFe_2O_4$, MnO, $Mn_3O_4$, $Co_3O_4$, Ni, $TiO_2$, $Al_2O_3$, CdSe, PbSe, $ZrO_2$, ZnO, Au, Ag, and graphene oxide.

* * * * *